(12) United States Patent
Stenhuus et al.

(10) Patent No.: US 8,569,024 B2
(45) Date of Patent: Oct. 29, 2013

(54) PRODUCTION OF STILBENOIDS

(75) Inventors: Bo Stenhuus, København Ø (DK); Hans Peter Smits, Holte (DK); Thomas Durhuus, København NV (DK); Michael Katz, Malmö (SE)

(73) Assignee: Evolva SA, Reinach (CH)

( * ) Notice: Subject to any disclaimer, the term of this patent is extended or adjusted under 35 U.S.C. 154(b) by 221 days.

(21) Appl. No.: 12/936,830

(22) PCT Filed: Apr. 2, 2009

(86) PCT No.: PCT/EP2009/053974
§ 371 (c)(1),
(2), (4) Date: Dec. 30, 2010

(87) PCT Pub. No.: WO2009/124879
PCT Pub. Date: Oct. 15, 2009

(65) Prior Publication Data
US 2011/0124067 A1    May 26, 2011

(30) Foreign Application Priority Data
Apr. 7, 2008 (GB) .................................. 0806256.4

(51) Int. Cl.
*C12P 7/22* (2006.01)
*C12N 1/00* (2006.01)

(52) U.S. Cl.
USPC .................. 435/156; 435/254.11; 435/254.2

(58) Field of Classification Search
USPC .................................. 435/156, 254.11, 254.2
See application file for complete search history.

(56) References Cited

U.S. PATENT DOCUMENTS

2004/0234671 A1    11/2004    Ector et al.

FOREIGN PATENT DOCUMENTS

| JP | 2001-008695 | 1/2011 |
| WO | WO2004/049832 | 6/2004 |
| WO | WO2006/089898 | 8/2006 |
| WO | WO2006/111163 | 10/2006 |
| WO | WO2008/009728 | 1/2008 |

OTHER PUBLICATIONS

Whisstock et al., Prediction of protein function from protein sequence. Q. Rev. Biophysics., 2003, vol. 36 (3): 307-340.*

Beekwilder, et al., "Production of Resveratrol in Recombinant Microorgansims", *Applied and Environmental Microbiology*, Aug. 2006, 5670-5672.
Becker et al, "Metabolic engineering of *Saccharomyces cerevisiae* for the synthesis of the wine related antioxidant resveratrol", *Fems Yeast Research*, 4, 2003, 79-85.
Berner, et al., "Genes and enzymes involved in caffeic acid biosynthesis in the actinomycete *Saccharothrix espanaensis*", J Bacteriol, 2006:188:2666-73.
Callemien, et al., "Hop as an interesting Source of Resveratrol for Brewers: . . . ", *J. Agric. Food Chem*, 2005, 53, 424-429.
Cochrane, et al., "The *Arabidopsis* phenylalanine ammonia lyase gene family: kinetic characterization of the four PAL isoforms", *Phytochemistry* 2004:65:1557-64.
Ehlting, et al., "Three 4-coumarate:coenzyme A ligases in *Arabidopsis thaliana* represent two evolutionarily divergent classes in angiosperms", *Plant J.*, 1999:19:9-20.
Gietz, et al., "Applications of high efficiency lithium acetate transformation of intact yeast cells using single-stranded nucleic acids as carrier", *Yeast*, 1991:7:253-63.
Gonzales-Candelas, et al., "The use of transgenic yeasts expressing a gene encoding a glycosyl hydrolase as a tool to increase resveratrol content in wine", *Inter Jnl of Food Microbiology* 59 (2000) 179-183.
Hain, et al., "Disease resistance results from foreign phytoalexin expression in a novel plant", *Nature*, 1993:361:153-6.
Hamberger, et al., "The 4-coumarate:CoA ligase gene family in *Arabidopsis thaliana* comprises one rare, sinapate-activating and three commonly occurring isoenzymes", *Proc Natl Acad Sci U S A*, 2004:101:2209-14.
Mizutani, et al., "Isolation of a cDNA and a genomic clone encoding cinnamate 4-hydroxylase from *Arabidopsis* and its expression manner in planta", *Plant Physiol*, 1997:113:755-63.
Mizutani, et al., "Two isoforms of NADPH:cytochrome P450 reductase in *Arabidopsis thaliana*. Gene structure, heterologous expression in insect cells, and differential regulation", *Plant Physiol.*, 1998:116:357-67.
Mumberg, et al., "Yeast vectors for the controlled expression of heterologous proteins in different genetic backgrounds", *Gene*, 1995:156:119-22.
Sikorski, et al., "A system of shuttle vectors and yeast host strains designed for efficient manipulation of DNA in *Saccharomyces cerevisiae*", *Genetics* 1989:122:19-27.
Verduyn, et al., "Effect of benzoic acid on metabolic fluxes in yeasts: a continuous-culture study on the regulation of respiration and alcoholic fermentation", *Yeast*, 1992:8:501-17.

* cited by examiner

*Primary Examiner* — Ganapathirama Raghu
(74) *Attorney, Agent, or Firm* — McDonnell Boehnen Hulbert & Berghoff LLP

(57) ABSTRACT

A method for the production of a stilbenoid, such as resveratrol or pinosylvin, by fermenting plant material such a grape must using a yeast having a metabolic pathway producing said stilbenoid, separating a solids waste material from said fermentation and extracting said stilbenoid.

9 Claims, 4 Drawing Sheets

PRODUCTION OF STILBENOIDS

The present invention relates to the production of stilbenoids by extraction thereof from wine making waste.

A number of strains of yeast which have been genetically engineered to produce one or more stilebenoids such as resveratrol and pinosylvin have been described. Thus, South African Patent 2004/8194 (University of Stellenbosch) and Becker et al disclosed a *Saccharomyces cerevisiae* for fermenting wine must having introduced therein a coumarate-coenzyme-A ligase encoding gene (4CL216) and a grapevine resveratrol synthase gene (vst1). WO2006/089898 disclosed a *Saccharomyces cerevisiae* also having introduced therein a gene encoding a phenylalanine or tyrosine-ammonia lyase (PAL/TAL) and a gene encoding a cinnamate 4-hydroxylase (C4H). WO2006/125000 discloses oleaginous cells having resveratrol production capacity. WO2008/009728 discloses a pinosylvin producing *Saccharomyces cerevisiae* having introduced therein a PAL, 4-coumarate CoA-ligase or cinnamate-CoA ligase, a pinosylvin synthase.

The extraction of resveratrol from grape seed and skin (marc) of red wine grapes has been proposed (Australian Harvest—Press release).

Beeckwilder et al disclose resveratrol production by a genetically engineered yeast and detection of resveratrol in the liquid culture medium. It was stated that resveratrol accumulated in the medium rather than in the cells.

Pretorius disclosed the possibility of developing wine yeasts producing resveratrol but indicated that the chances of success were unknown.

Becker et al disclosed a genetically modified yeast which produced glycosylated resveratrol during fermentation of a culture medium containing coumaric acid, and discussed the possibility of fermenting grapes with such a modified yeast in the hope of producing wine containing more than a normal level of resveratrol. Glycosylated resveratrol production was demonstrated by extraction from yeast cells grown in culture medium.

Further sources of stilbenoids are desirable. There is now provided according to the present invention a method for the production of a stilbenoid, comprising extracting said stilbenoid from a solids waste material separated from a fermentation of plant material conducted using a yeast having a metabolic pathway producing said stilbenoid.

The term 'solids waste material' refers to a waste material containing undissolved solids, optionally with significant quantities of free liquid such that the waste material may be flowable or not, including pastes or slurries as well as embracing dry solids. 'Waste material' includes any material that is not the desired end product of the fermentation (which will typically be wine or beer of some form) and includes residual plant material mixed with yeast cells (live or dead).

The method may further comprise the preliminary steps of conducting said fermentation of plant material using a said yeast having a metabolic pathway producing said stilbenoid and separating a solids waste material from said fermentation. The solids waste material may comprise yeast solids and plant material solids.

Preferably, the fermentation is a fermentation of fruit must together with or separated from pommace or is a fermentation of pommace separated from fruit must. The fruit may for instance be grape, apple or pear. The fermentation may be a beer making fermentation, all forms of beer being included, whether obtained by the use of a top fermenting yeast or a bottom fermenting yeast.

Methods for extracting stilbenoids, including resveratrol and pinosylvin, are described in the above publications. Suitable solvents include esters such as ethyl acetate or a solvent as described in GB 0714671.5, i.e. an ester which preferably is of the general formula $R^6$—COO—$R^7$, and $R^6$ is H or an aliphatic straight or branched chain hydrocarbon moiety of from 1-6 carbon atoms and $R^7$ is an aliphatic straight or branched chain hydrocarbon moiety of from 2-16 carbon atoms, or a heteroatom containing hydrocarbon moiety of from 2 to 16 carbon atoms or an aromatic or heteroaromatic moiety of from 5 to 16 carbon atoms. $R^7$ may have from 3 to 9 carbon atoms. $R^6$ may have from 1 to 4 carbon atoms.

Preferably, said ester is an octyl acetate, especially n-octyl acetate.

Optionally, said liquid comprises or further comprises an alkane. It may consist of a said alkane and a said ester. Said alkane may be a $C_6$ to $C_{16}$ straight or branched chain alkane, e.g. a $C_{9-14}$ alkane, e.g. a $C_{12}$ alkane. Preferably, said alkane is n-dodecane.

The stilbenoid producing yeast may be as described in any of the above publications or genetically engineered according to the principles or practice there described. In particular, it may be a resveratrol producing yeast as described generally or by way of example in WO2006/089898 or a pinosylvin producing yeast as described generally or by way of example in WO2008/009728.

Preferably therefore, the yeast may be one having an operative metabolic pathway comprising at least one enzyme activity, said pathway producing 4-coumaric acid and producing resveratrol therefrom, or an oligomeric or glycosidically-bound derivative thereof preferably by a reaction catalysed by an enzyme in which endogenous malonyl-CoA is a substrate. Preferably the resveratrol is produced from 4-coumaroyl-CoA by a resveratrol synthase expressed in said micro-organism from nucleic acid coding for said enzyme which is not native to the yeast.

The 4-coumaric acid may be produced from trans-cinnamic acid by a cinnamate 4-hydroxylase not native to the yeast.

4-coumaric acid may be produced from tyrosine in a reaction catalysed by a L-phenylalanine ammonia lyase or a tyrosine ammonia lyase not native to the yeast. Trans-cinnamic acid may be produced from L-phenylalanine in a reaction catalysed by a L-phenylalanine ammonia lyase not native to the yeast. 4-coumaroyl-CoA may be formed in a reaction catalysed by a 4-coumarate-CoA ligase introduced into the yeast.

A native NADPH:cytochrome P450 reductase (CPR) may be expressed in the yeast or may recombinantly introduced.

Thus, the yeast may be one containing one or more copies of an heterologous DNA sequence encoding phenylalanine ammonia lyase operatively associated with an expression signal, and containing one or more copies of an heterologous DNA sequence encoding cinnamate-4-hydroxylase operatively associated with an expression signal, and containing one or more copies of an heterologous DNA sequence encoding 4-coumarate CoA-ligase operatively associated with an expression signal, and containing one or more copies of an heterologous DNA sequence encoding resveratrol synthase operatively associated with an expression signal, or may be one lacking cinnamate-4-hydroxylase activity, and containing one or more copies of a heterologous DNA sequence encoding tyrosine ammonia lyase operatively associated with an expression signal, and containing one or more copies of an heterologous DNA sequence encoding 4-coumarate CoA-ligase operatively associated with an expression signal, and containing one or more copies of an heterologous DNA sequence encoding resveratrol synthase operatively associated with an expression signal.

For the production of pinosylvin, the yeast may have an operative metabolic pathway comprising at least one enzyme activity, said pathway producing pinosylvin from cinnamic acid and preferably producing cinnamic acid and produces pinosylvin therefrom. Said pinosylvin may be produced in a reaction catalysed by an enzyme in which endogenous malonyl-CoA is a substrate, suitably from cinnamoyl-CoA by a stilbene synthase, suitably expressed in the yeast from nucleic acid coding for said enzyme which is not native to the yeast.

Cinnamic acid is preferably produced in said pathway from L-phenylalanine in a reaction catalysed by a L-phenylalanine ammonia lyase (PAL) which may be not native to the yeast.

Said PAL is preferably one accepting phenylalanine as a substrate and producing cinnamic acid therefrom, such that if the PAL also accepts tyrosine as a substrate and forms coumaric acid therefrom, the ratio Km(phenylalanine)/Km(tyrosine) for said PAL is less than 1:1 and preferably such that the ratio $K_{cat}(PAL)/K_{cat}(C4H)$ is at least 2:1.

Cinnamoyl-CoA may be formed in a reaction catalysed by a 4-coumarate-CoA ligase or a cinnamoyl-CoA ligase which may be not native to the yeast.

Any or all of at least one copy of a genetic sequence encoding a phenylalanine ammonia lyase, at least one copy of a genetic sequence encoding a 4-coumarate-CoA ligase or cinnamate-CoA ligase, at least one copy of a genetic sequence encoding a resveratrol synthase or a pinosylvin synthase may be present operatively linked to an expression signal not natively associated with said genetic sequence.

Thus the yeast may be one containing one or more copies of an heterologous DNA sequence encoding phenylalanine ammonia lyase operatively associated with an expression signal, and containing one or more copies of an heterologous DNA sequence encoding 4-coumarate CoA-ligase or cinnamate-CoA ligase operatively associated with an expression signal, and containing one or more copies of an heterologous DNA sequence encoding resveratrol synthase operatively associated with an expression signal or may be one containing one or more copies of an heterologous DNA sequence encoding phenylalanine ammonia lyase operatively associated with an expression signal, and containing one or more copies of an heterologous DNA sequence encoding 4-coumarate CoA-ligase or cinnamate-CoA ligase operatively associated with an expression signal, and containing one or more copies of an heterologous DNA sequence encoding pinosylvin synthase operatively associated with an expression signal.

In all cases, expression of the gene ACC1 may be boosted to increase the pool of malonyl-CoA available in the metabolic pathway.

The yeast may be of the genus *Saccharomyces* and may be of the species *Saccharomyces cerevisiae, S. kluyveri, S. bayanus, S. exiguus, S. sevazzi,* or *S. uvarum* or others, especially any conventionally used in brewing or wine making.

The accompanying drawings show results obtained in the examples as follows.

Figure 1:
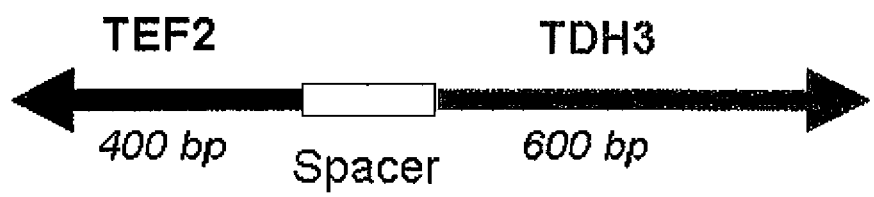
FIG. 1 shows a divergent fusion fragment formed between a TEF2 promoter and TDH3 promoter.
Figure 2:
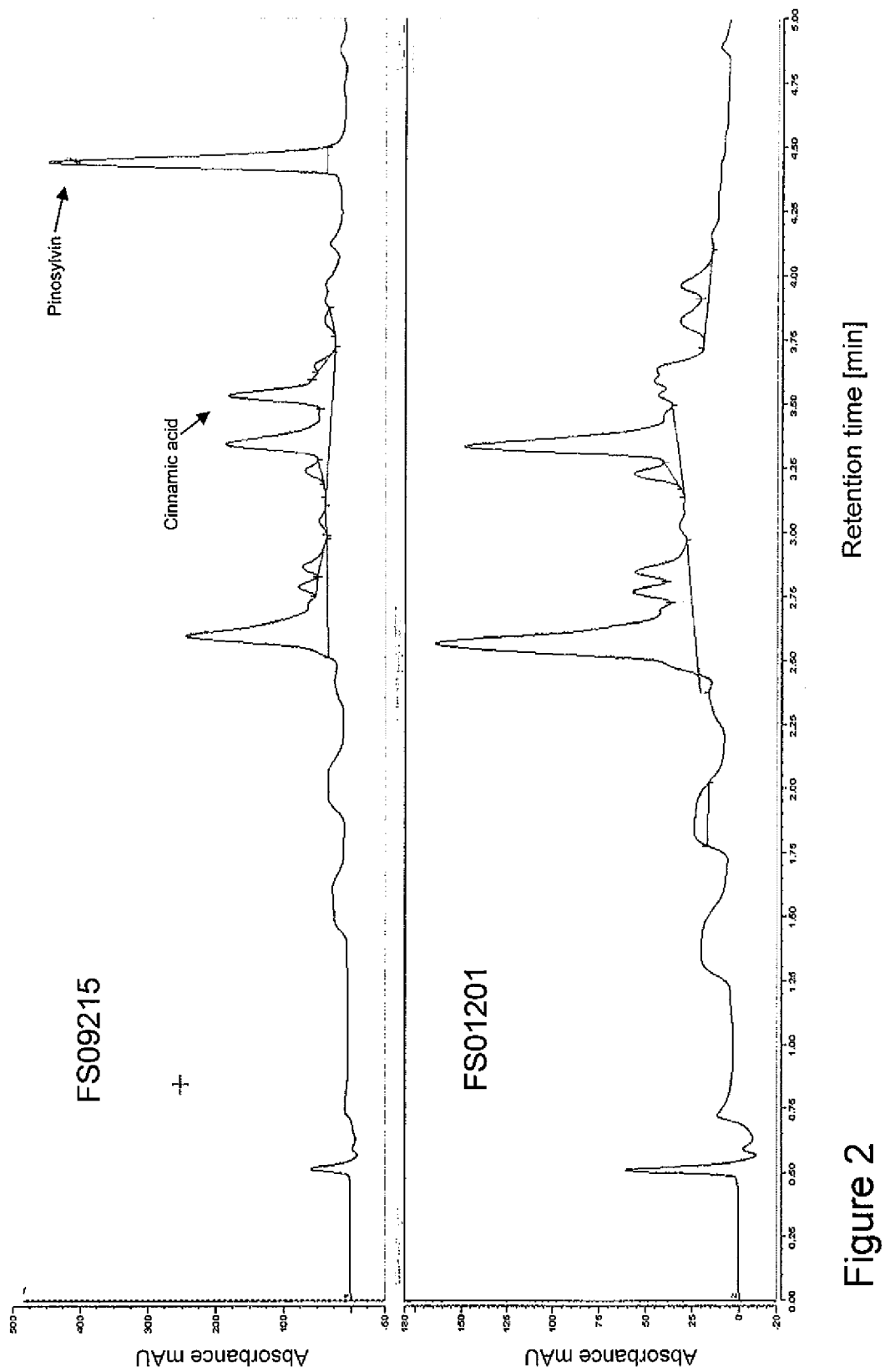
FIG. 2 shows HPLC chromatograms of pulp extract obtained in Example 14 with Absorbance plotted against retention time.
Figure 3:
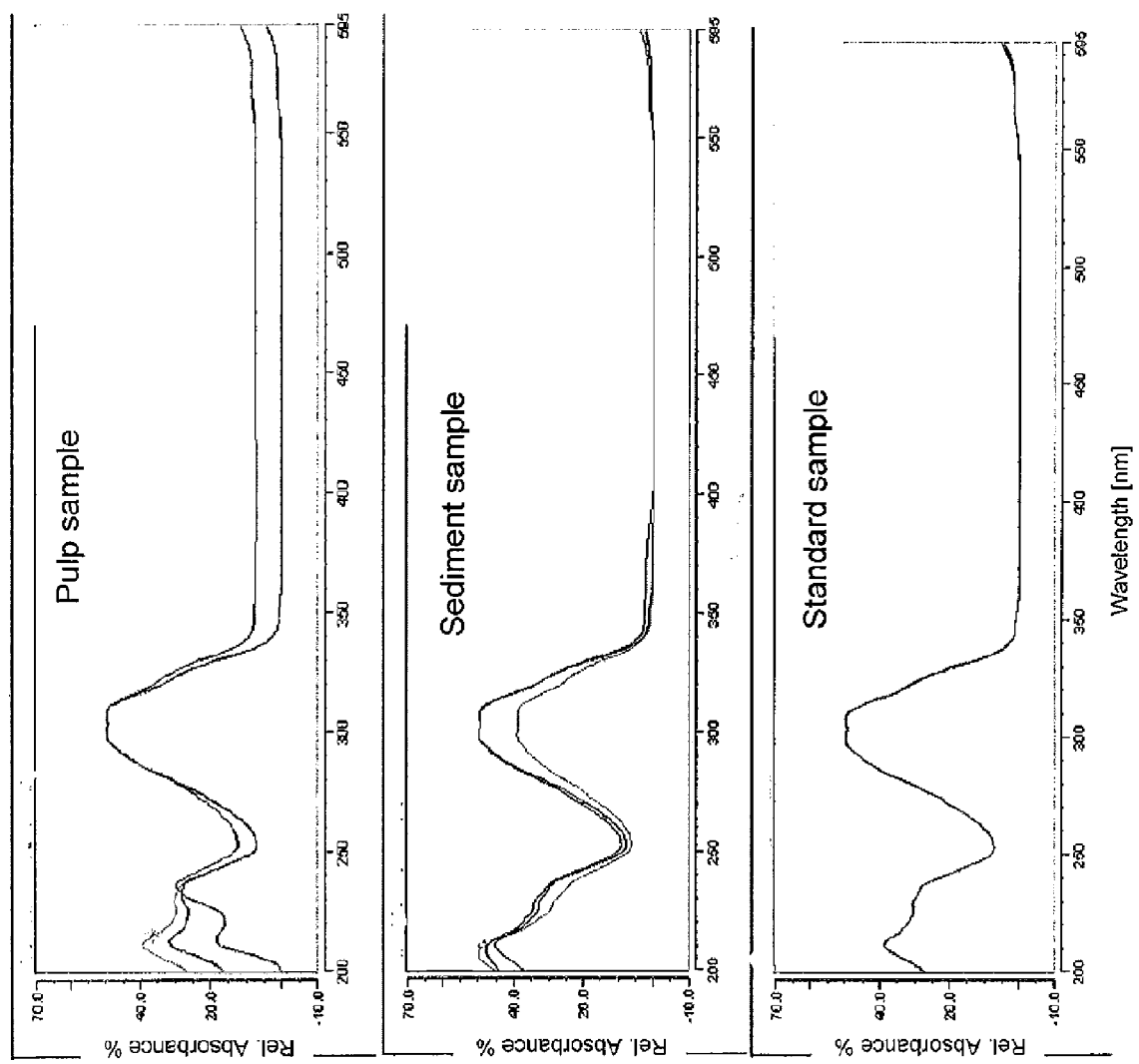
FIG. 3 shows further chromatograms obtained in Example 14 showing UV spectra of pinosylvin peaks in waste stream extracts (pulp sample and sediment sample) and of a standard.
Figure 4:
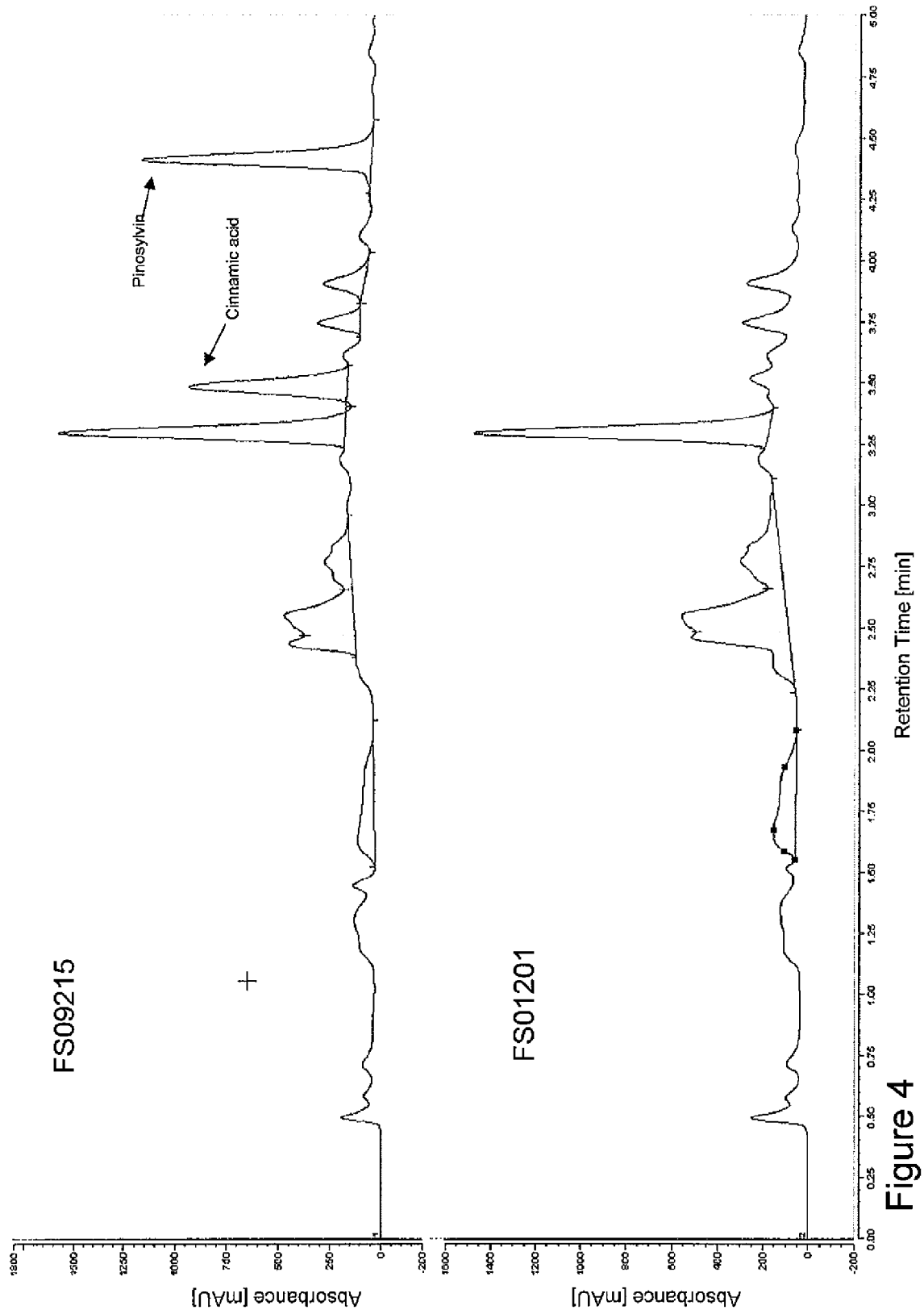
FIG. 4 shows still HPLC chromatograms of sediment obtained in Example 14 with Absorbance plotted against retention time.

The invention will be illustrated by the following non-limiting examples.

EXAMPLES

Example 1

Isolation of Genes Encoding PAL2, C4H, AR2, 4CL and VST1

Phenylalanine ammonia lyase (PAL2) (Cochrane et al., 2004) (SEQ ID NO 1), cinnamate 4-hydroxylase (C4H) (Mizutani et al, 1997) (SEQ ID NO 2), cytochrome P450 reductase (AR2)(Mizutani and Ohta, 1998) (SEQ ID NO 3), 4-coumarate:coenzymeA ligase (4CL) (Hamberger and Hahlbrock 2004; Ehlting et al., 1999) (SEQ ID NO 4) were isolated via PCR from *A. thaliana* cDNA (BioCat, Heidelberg, Germany) using the primers in table 1.

The codon optimized VST1 gene encoding *Vitis vinifera* (grapevine) resveratrol synthase (Hain et al., 1993) (SEQ ID NO 5) for expression in *S. cerevisiae* was synthesized by GenScript Corporation (Piscataway, N.J.). The synthetic VST1 gene was delivered inserted in *E. coli* pUC57 vector flanked by BamH1 and Xho1 restriction sites. The synthetic gene was purified from the pUC57 vector by BamH1/Xho1 restriction and purified from agarose gel using the QiaQuick Gel Extraction Kit (Qiagen).

TABLE 1

| Primer for amplification of gene (Restriction sites are underlined) | Gene |
|---|---|
| 5-CG <u>GAATTC</u> <u>CGTACG</u> TA ATG GAT CAA ATC GAA GCA ATG TT<br>SEQ ID NO: 10 | PAL2 |
| 5-CG <u>ACTAGT</u> TTA GCA AAT CGG AAT CGG AGC<br>SEQ ID NO: 11 | PAL2 |
| 5-CG <u>CTCGAG</u> GCGGCCGC TAAAAT ATG GAC CTC CTC TTG CTG GAG<br>SEQ ID NO: 12 | C4H |
| 5-AGTAGATGGAGTAGATGGAGTAGATGGAGTAGATGG ACA GTT CCT TGG TTT CAT AAC G<br>SEQ ID NO: 13 | C4H |
| 5-CCATCTACTCCATCTACTCCATCTACTCCATCTACT AGG AGA TCC GGT TCT GGG A<br>SEQ ID NO: 14 | AR2 |
| 5-CG GGTACCAT TTA CCA TAC ATC TCT AAG ATA TCT TCC<br>SEQ ID NO: 15 | AR2 |
| 5' GC<u>GAATTC</u>TTATGACGACACAAGATGTGATAGTCAATGAT<br>SEQ ID NO: 16 | 4CL |
| 5' GC<u>ACTAGT</u>ATCCTAGTTCATTAATCCATTTGCTAGTCTTGC<br>SEQ ID NO: 17 | 4CL |

The coding sequence of tyrosine ammonia lyase (TAL) from *Rhodobacter capsulatus* (Kyndt et al., 2002; is codon optimized for expression in *S. cerevisiae* using the online service backtranslation tool at www.entelechon.com, yielding sequence SEQ ID NO: 6)

Example 2

Construction of a Yeast Vector for Galactose Induced Expression of PAL2 and C4H:AR2 Fusion Gene The gene encoding PAL2 was amplified from cDNA from *A. thaliana* as template using forward primer 5-CG <u>GAATTC</u>

CGTACG TA ATG GAT CAA ATC GAA GCA ATG TT-3 SEQ ID NO 29 and reverse primer 5-CG ACTAGT TTA GCA AAT CGG AAT CGG AGC-3 SEQ ID NO 30. The amplified PAL2 PCR-product was digested with EcoR1/Spe1 and ligated into EcoR1/Spe1 digested pESC-URA vector (Stratagene), resulting in vector pESC-URA-PAL2. Two different clones of pESC-URA-Pal2 were sequenced to verify the sequence of the cloned gene.

C4H was amplified using cDNA from *A. thaliana* as template using forward primer 5-CG CTCGAG GCGGCCGC TAAAAT ATG GAC CTC CTC TTG CTG GAG-3 SEQ ID NO 31 and reverse primer 5-AGTAGATGGAGTAGATG-GAGTAGATGGAGTAGATGG ACA GTT CCT TGG TTT CAT AAC G-3 SEQ ID NO 32. AR2 was amplified using cDNA from *A. thaliana* as template using forward primer 5-CCATCTACTCCATCTACTCCATCTACTCCATCTACT AGG AGA TCC GGT TCT GGG A-3 SEQ ID NO 33 and reverse primer 5'-CG GGTACCAT TTA CCA TAC ATC TCT AAG ATA TCT TCC-3 SEQ ID NO 34.

The amplified PCR products C4H and AR2 were used as templates for the creation of the fusion gene C4H:AR2 using the forward primer 5-CG CTCGAG GCGGCCGC TAAAAT ATG GAC CTC CTC TTG CTG GAG-3 SEQ ID NO 35 and the reverse primer 5-CG GGTACC AT TTA CCA TAC ATC TCT AAG ATA TCT TCC-3 SEQ ID NO 36.

The fusion gene C4H:AR2 gene was digested with XhoI/KpnI and ligated into XhoI/KpnI digested pESC-URA-PAL2. The resulting plasmid, pESC-URA-PAL2-C4H:AR2, contained the genes encoding PAL2 and C4H:AR2 under the control of the divergent galactose induced <=GAL1/GAL10=> promoters. The sequence of the gene encoding C4H:AR2 was verified by sequencing of two different clones of pESC-URA-PAL2-C4H:AR2.

Example 3

Construction of a Yeast Vector for Galactose Induced Expression of 4CL1 and VST1

The gene encoding 4CL was isolated as described in example 1. The amplified 4CL PCR-product was digested with EcoR1/Spe1 and ligated into EcoR1/Spe1 digested pESC-HIS vector (Stratagene), resulting in vector pESC-HIS-4CL.

Two different clones of pESC-HIS-4CL were sequenced to verify the sequence of the cloned gene.

The gene encoding VST1 was isolated as described in example 1. The amplified synthetic VST1 gene was digested with BamH1/Xho1 and ligated into BamH1/Xho1 digested pESC-HIS-4CL. The resulting plasmid, pESC-HIS-4CL-VST1, contained the genes encoding 4CL and VST1 under the control of the divergent galactose induced <=GAL1/GAL10=> promoters. The sequence of the gene encoding VST1 was verified by sequencing of two different clones of pESC-HIS-4CL-VST1.

Example 4

Construction of Strong Constitutive Promoter Fragment TDH3

The 600 base pair TDH3 (GPD) promoter was amplified from *S. cerevisiae* genomic DNA using the forward primer 5'GC GAGCTC AGT TTA TCA TTA TCA ATA CTC GCC ATT TCA AAG SEQ ID NO: 18 containing a Sac1 restriction site and the reverse primer 5'-CG TCTAGA ATC CGT CGA AAC TAA GTT CTG GTG TTT TAA AAC TAA AA SEQ ID NO: 19 containing a Xba1 restriction site. The amplified TDH3 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TDH3.

Example 5

Construction of Constitutive Strong Promoter Fragment TEF2

The 400 base pair TEF2 promoter was amplified from *S. cerevisiae* genomic DNA using the forward primer 5'-GC GAGCTC ATA GCT TCA AAA TGT TTC TAC TCC TTT TTT ACT CTT SEQ ID NO: 20 containing a Sac1 restriction site and the reverse primer 5'-CG TCTAGA AAA CTT AGA TTA GAT TGC TAT GCT TTC TTT CTA ATG A SEQ ID NO: 21 containing a Xba1 restriction site. The amplified TEF2 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TEF2.

Example 6

Construction of Fused Divergent Constitutive TEF and TDH3 Promoter Fragment

A divergent fusion fragment (FIG. 1) between TEF2 promoter and TDH3 promoter was constructed starting from PRS416-TEF and PRS416-TDH3.

The 600 base pair TDH3 fragment was reamplified from PRS416-TDH3 using the forward primer 5' TTGCGTATTGGGCGCTCTTCC GAG CTC AGT TTA TCA TTA TCA ATA CTC GC SEQ ID NO: 22 containing the underlined overhang for fusion PCR to TEF2 fragment and the reverse primer 5' AT GGATCC TCT AGA ATC CGT CGA AAC TAA GTT CTG SEQ ID NO: 23 containing the underlined BamH1 restriction site. This resulted in a fragment ready for fusion to the below TEF2 fragment.

The 400 base pair TEF2 fragment including a 277 base pair spacer upstream of the Sac1 restriction site was reamplified from PRS416-TEF2 using the forward primer 5' AT GAATTC TCT AGA AAA CTT AGA TTA GAT TGC TAT GCT TTC SEQ ID NO: 24 containing the underlined EcoR1 restriction site and the reverse primer 5' TGATAATGATAAACTGAGCTC GGA AGA GCG CCC AAT ACG CAA AC SEQ ID NO: 25 containing the underlined overhang for fusion to the TDH3 fragment. This resulted in a 680 base pair fragment ready for fusion to the TDH3 fragment.

The 680 base pair TEF2 fragment and the 600 base pair TDH3 fragments were joined together (fused) using fusion PCR with the forward primer 5' AT GAATTC TCT AGA AAA CTT AGA TTA GAT TGC TAT GCT TTC SEQ ID NO 37 and the reverse primer 5' AT GGATCC TCT AGA ATC CGT CGA AAC TAA GTT CTG SEQ ID NO: 26, resulting in the divergent fragment <=TEF2/TDH3=> (Sequence ID NO 7).

Example 7

Construction of a Yeast Vector for Constitutive Expression of PAL2 and C4H:AR2 Fusion Gene The vector pESC-URA-PAL2-C4H:AR2 with divergent galactose inducible promoters GAL1/GAL10 was sequentially digested with NotI and BsiWI to remove the GAL1/GAL10 promoters.

The divergent constitutive <=TEF2/TDH3=> promoter fragment (Example 6) was re-amplified with forward primer 5-GC CGTACG TCT AGA AAA CTT AGA TTA GAT TGC TAT GCT TTC-3 SEQ ID NO: 27 and reverse primer 5-ATT GCGGCCGC TCT AGA ATC CGT CGA AAC TAA GTT CTG-3 SEQ ID NO: 28. The resulting PCR product was sequentially digested with NotI and BsiWI and ligated into the above vector without the GAL1/Gal10 fragment. This resulted in a vector pESC-URA-TEF-PAL2-TDH3-C4H: AR2 with replaced promoters, from GAL1/Gal10 to TEF2/TDH3 Sequence ID NO 8).

Example 8

Construction of a Yeast Vector for Constitutive Expression of a TAL Gene

The vector pESC-URA-TAL with divergent galactose inducible promoters GAL1/GAL10 is sequentially digested with EcoRI and BamHI to remove the GAL1/GAL10 promoters.

The divergent constitutive <=TEF2/TDH3=> promoter fragment (Example 6) was sequentially digested with EcoR1 and BamH1 and ligated into the above BamHI/EcoRI linearized pESC-URA-TAL vector without the GAL1/GAL10 fragment. This resulted in a vector pesc-URA-TEF-TAL with replaced promoters, from GAL1/Gal10 to TEF2/TDH3.

Example 9

Construction of a Yeast Vector for Constitutive Expression Induced of 4CL and VST1

The vector pESC-HIS-4CL-VST1 with divergent galactose inducible promoters GAL1/GAL10 was sequentially digested with EcoR1 and BamH1 to remove the GAL1/GAL10 promoters.

The divergent constitutive <=TEF2/TDH3=> promoter fragment (Example 6) was sequentially digested with EcoR1 and BamH1 and ligated into the above linearized vector without the GAL1/GAL10 fragment. This resulted in a vector pesc-HIS-TEF2-4CL-TDH3-VST1 with replaced promoters, from GAL1/Gal10 to TEF2/TDH3 SEQ ID NO 9).

Example 10

Generation of a Strain with Constitutive Expression of the Phenylpropanoid Pathway from Phenylalanine to Resveratrol in the Yeast S. cerevisiae.

The transformation of the yeast cell was conducted in accordance with methods known in the art, for instance by using lithium acetate transformation method (Gietz and Schiestl, 1991). S. cerevisiae strain FS01528 (CEN.PK MATa ura3 His3) was co-transformed with pESC-URA-TEF-PAL2-TDH3-C4H:AR2 (example 7) and pesc-HIS-TEF2-4CL-TDH3-VST1 (example 9), and the transformed strain was named FS09215. Transformants were selected on medium lacking uracil and histidine and streak purified on the same medium.

Example 11

Generation of a Strain with Constitutive Expression of the Phenylpropanoid Pathway from Tyrosine to Resveratrol in the Yeast S. cerevisiae.

The transformation of the yeast cell is conducted in accordance with methods known in the art, for instance by using lithium acetate transformation method (Gietz and Schiestl, 1991). S. cerevisiae strain FS01528 (CEN.PK MATa ura3 His3) is co-transformed with pESC-URA-TEF-TAL (example 8) and pesc-HIS-TEF2-4CL-TDH3-VST1 (example 9), to obtain strain TEF2-TAL-TEF2-4CL-TDH3-VST1. Transformants are selected on medium lacking uracil and histidine and streak purified on the same medium.

Example 12

HPLC Determination of Stilbenoids, Phenylpropanoids and Ethanol.

For quantitative analysis of cinnamic acid, trans-resveratrol and trans-pinosylvin, samples were subjected to separation by high-performance liquid chromatography (HPLC) Agilent Series 1100 system (Hewlett Packard) prior to uv-diode-array detection at $\lambda=306$ nm. A Phenomenex (Torrance, Calif., USA) Luna 2.5 micrometer C18 (100×2.00 mm) column was used at 60° C. As mobile phase a non linear S-shaped gradient of acetonitrile and milliQ water (both containing 50 ppm trifluoroacetic acid) was used at a flow of 0.8 ml/min. The S-shaped gradient profile was from 10% to 100% acetonitrile in 5 minutes. The elution time was approximately 3.0 minutes for trans-resveratrol and 4.4 minutes trans-pinosylvin. Pure pinosylvin standard (>95% pure) was purchased from ArboNova (Turku, Finland) and pure trans-resveratrol standard was purchased from Sigma.

The grape-must was analysed for the content of ethanol by HPLC using an Aminex HPX-87H ion-exclusion column (Bio-Rad, Hercules, Calif.) at 60° C., with 5 mM $H_2SO_4$ as a mobile phase at a flow rate of 0.6 ml/min. The ethanol was detected by a refractometer (Shodex RI-71).

Example 13

Generation of Biomass

Yeast strains FS01201 (CEN.PK 113-7D wild type non modified control strain) was kept on YPD agar plates with 20 g/l glucose. FS09215 (genetically modified resveratrol producer from example 10) was kept on SC-HIS-URA agar plates with 20 g/l glucose.

The two yeast strains were grown in 10-16 500 ml shake flasks with 200 ml DELFT medium (Verduyn et al, 1992) containing 45 g/l glucose, 30 g/l ammonium sulphate, 14 g/l $KH_2PO_4$, and 1.5 g/l $MgSO_4$ for 4 days at 30° C. and 150 rpm. A paste of wet weight cells was collected (harvested) by centrifugation at 3000 g for 5 minutes in 50 ml Sartorious tubes and discarding the supernatant after each round. After repetitive rounds of centrifugation 26 g wet weight was collected of strain FS01201 and 24 g wet weight of FS09215.

Example 14

Production of Red Wine from Grapes using a S. cerevisiae Strain with Constitutive Expression of the Phenylpropanoid Pathway from Phenylalanine to Resveratrol.

Commercially available seedless "Crimson" grapes (product of Brazil), were used to produce two red wine's: a control wine produced by using strain FS01201 and a stilbenoid-enriched wine by using strain FS09215 as described in example 10. Said strain harbours a phenylpropanoid pathway comprising an oxygen-dependent cinnamate-4-hydroxylase (C4H) that converts cinnamic-acid in coumaric-acid. Hence, under the oxygen-deprived conditions that typically prevail in the anaerobic fermentation-process used for wine-making, said strain can only produce resveratrol if endogenous coumaric acid is present in the grape-pulp and grape-must. With a lack of sufficient oxygen, however, said strain has the potential of producing pinosylvin, that is derived from cinnamic acid.

Preparation of Starter Culture

A starter culture of strain FS01201 and FS09215 was prepared by crushing 2 kilo's of grapes and filtering the resulting grape pulp with a loose-woven cotton cloth (cheesecloth) and subsequently collecting the grape juice in a sterile open plastic bucket. An aliquot of 500 ml of grape juice was enriched with 40 grams of glucose and divided into two aliquots of 250 ml that were transferred to two sterile 500 ml-shakeflasks. The shakeflasks were inoculated with approximately 2 grams wet-weight of cells from either FS01201 or FS09215 as prepared according to example 13, and incubated for approximately 24 hours at room temperature. Activity of yeast was indicated by formation of $CO_2$ resulting in a foam-layer.

Primary Pulp Fermentation

A pulp of grapes was prepared by disrupting 16 kilo's of grapes with a semi-professional kitchen blender. The resulting grape-pulp was enriched with approximately 2 coffee-spoons of "yeast nutrient" (stimulates yeast growth) and 3 coffee-spoons of "pecto-enzymes" (breaks down pectin in the grape skin). Both the pecto-enzymes and yeast nutrient were part of a commercially available wine-making kit. Said enriched grape-pulp was divided into two equal aliquots, approximately 7 to 8 liter each, and transferred into two 10 liter plastic round sterilized containers that were open at the top. A pulp-fermentation was initiated by adding the total amount of 250 ml of starter culture to the grape pulp, and mixing it well together with a large spoon; one bucket was inoculated with FS01201, and the other with FS09215. The progression of the pulp-fermentation was visually monitored on a daily basis, and the appearance of a foam-layer on the top, caused by $CO_2$ formation, indicated that the fermentation was successfully ongoing. The $CO_2$ formation caused the grape-pulp to float on top of the grape-juice, and therefore the pulp was mixed with a large spoon on a daily basis as well. Formation of foam ceased after 9 days, and the grape-pulp "fluidized", which indicated that almost al grape-sugars were consumed and the pulp-fermentation was near its end. The grape pulp, therefore, was separated from the liquid fraction (containing the juice and the yeast, i.e. the grape-must) by using a cheesecloth. For each strain approximately 5.5 to 6 liter of grape-must was collected. The fermented juice was analyzed for the content of alcohol and stilbenoids. The FS01201- and FS09215 grape-must contained 84.01 g/l (i.e. 10.6 vol %) of ethanol and 79.65 g/l (i.e. 10.1 vol %) respectively. The development of ethanol formation during the pulp fermentation is listed in table 2 below.

TABLE 2

Ethanol formation in primary pulp fermentation

| | FS01201 | | FS09215 | |
| --- | --- | --- | --- | --- |
| | g/l | vol % | g/l | vol % |
| Day 6 | 69.87 | 8.86 | 68.72 | 8.71 |
| Day 7 | 83.69 | 10.61 | 81.8 | 10.37 |
| Day 8 | 81.44 | 10.32 | 81.68 | 10.35 |
| Day 9 | 84.01 | 10.65 | 79.65 | 10.10 |

Furthermore, no stilbenoids were found in either grape-must, however, low levels of cinnamic acid (1.05 mg/l) were determined in the FS09215 grape-must. For the FS01201 and FS09215 pulp-fermentation, a total of 1757 grams and 1780 grams wet-weight of grape-pulp was collected respectively. The grape pulp and approximately 1.5 liter of the remaining grape-must were stored at 4° C.

Secondary Grape-Must Fermentation

The fermentation was now continued with the grape-must. In order to enhance the alcohol percentage to a level that is usually found in commercial red wines (12- to 15 vol %), an aliquot of 3.5 liter of grape-must of either pulp fermentation was enriched with approximately 340 g of commercially available sugar ("Dansukker", dissolved and heated in approximately 300 ml of water). The addition of the extra sugar caused a dilution of the grape-must, resulting in a slight reduction of ethanol titers. Said enriched grape-must was transferred to a 5 liter glass-bottle that was stoppered with a "water-lock" to enable release of CO2, but at the same time preventing contamination. After 4 days the ethanol concentration rose to 99.46 g/l (i.e. 12.6 vol %) and 102.78 g/l (i.e. 13.0 vol %). To enhance the ethanol concentration even further, a second addition was made: 150 grams of sugar ("Dansukker") was dissolved into 1400 ml of the previously stored non-enriched grape-must, which was then subsequently added to the fermentation glass-bottle. The total volume of the grape-must was now approximately 5 liters, and with that almost completely filled the glass bottle leaving no room for air in the top of the bottle. The addition of the extra sugar caused a dilution of the grape-must, resulting in a slight reduction of ethanol titers. After a further 8 days, foam formation (i.e. $CO_2$ formation) ceased completely, indicating that the fermentation was finished and that all sugars were depleted. The final ethanol concentration was 116.06 g/l (i.e. 14.7 vol %) and 109.64 g/l (i.e. 13.9 vol %), as listed in table 3.

TABLE 3

Ethanol-, phenylpropanoid- and stilbenoid formation in secondary grape-must fermentation

| | FS01201 | | FS09215 | | | |
| --- | --- | --- | --- | --- | --- | --- |
| | | | | | cinnamic | |
| | ethanol (g/l) | ethanol (vol %) | ethanol (g/l) | ethanol (vol %) | acid (mg/l) | pinosylvin (mg/l) |
| Day 10 | 82.39 | 10.44 | 85.21 | 10.80 | 1.19 | 0.62 |
| Day 11 | 91.52 | 11.60 | 91.72 | 11.62 | 1.51 | 0.62 |
| Day 12 | 99.73 | 12.64 | 98.2 | 12.45 | not analyzed | not analyzed |
| Day 13 | 99.46 | 12.61 | 102.78 | 13.03 | not analyzed | not analyzed |
| Day 14 | 97.58 | 12.37 | 92.04 | 11.67 | 1.36 | 0.57 |
| Day 15 | 98.21 | 12.45 | 96.06 | 12.17 | not analyzed | not analyzed |
| Day 16 | 108.07 | 13.70 | 100.86 | 12.78 | 1.64 | 0.57 |
| Day 17 | 109.45 | 13.87 | 104.22 | 13.21 | 1.72 | 0.60 |
| Day 18 | 120.48 | 15.27 | 111.6 | 14.14 | 1.63 | 0.60 |
| Day 20 | 121.79 | 15.44 | 111.84 | 14.17 | 1.76 | 0.57 |
| Day 21 | 116.06 | 14.71 | 109.64 | 13.90 | 1.90 | 0.60 |

The reference strain FS01201 did neither produce phenylpropanoid-intermediates nor stilbenoids. The chromatograms of the grape-must of FS09215 contained a peak with a similar retention time as pinosylvin; indeed said peak with retention time of 4.4 minutes, displayed a UV-spectrum that was identical to pinosylvin. Similarly, the presence of cinnamic acid was confirmed as well. Quantification of the peaks indicated that the grape-must of strain FS09215 contained cinnamic acid and pinosylvin in final concentrations of 1.90 mg/l and 0.60 mg/l respectively (Table 3). Neither resveratrol nor coumaric acid could be detected, indicating that the activity of C4H was hampered by the anaerobic conditions. Furthermore, the lack of resveratrol and coumaric acid suggested that no endogenous coumaric acid was present in the grape-must of the "Crimson" grapes used for this experiment.

In both fermentations, sediment settled on the bottom, which likely composed of small-size particle grape-residues and yeast cells. Said sediment was isolated from the grape-must by siphoning, and approximately 300 ml could be collected for either fermentation. The sediments were stored at 4° C. until further analysis on stilbenoid content.

Analysis of Waste-Stream for the Presence of Stilbenoids

Approximately 125 grams of the grape pulp that was generated in the primary pulp fermentation was extracted over night with 30 ml of ethyl acetate (divided in three 50 ml Sartorious tubes) using a rotary unit at ambient temperature (24° C.). The extraction tubes were covered with aluminium foil to avoid any light induced degradation of stilbenoids. The following day the extraction mixture was centrifuged at 3800×g for 10 minutes, and the upper, yellow/greenish coloured, ethyl acetate was collected and pooled into one tube. From the initial 30 ml ethyl acetate, approximately 28 ml extract was collected for the FS1201 grape-pulp suspension, and 30 ml of ethyl acetate for the FS09215 grape-pulp suspension. Said ethyl acetate fractions were reduced in volume by evaporation for 2 hours, using a freeze dryer, until a dry residue was obtained.

The dry, dark coloured, residue was dissolved in 500 microliter 50% ethanol which resulted in a solution that contained non-dissolved dark precipitates. The solution was whirly-mixed and centrifuged at 13000×g for 5 minutes and the supernatant was diluted 5-fold with 50% ethanol. Said procedure resulted in a clear yellowish solution that could be used for HPLC analysis.

The grape-pulp of the control strain FS01201 did neither contain stilbenoids nor cinnamic- or coumaric acid (FIG. 6).

The chromatogram of the grape-pulp of FS09215 contained a peak with a similar retention time as pinosylvin; indeed said peak with retention time of 4.4 minutes, displayed a UV-spectrum that was identical to pinosylvin (FIGS. 6 and 7). Similarly, the presence of cinnamic acid was confirmed as well. Quantification of the peaks indicated that the grape-pulp contained cinnamic acid and pinosylvin in concentrations of 1.96 mg/kg pulp and 1.94 mg/kg pulp respectively. The total amount of grape-pulp recovered was 1780 grams, and can be considered as a primary waste-stream generated with the production of 5 liter red wine. Therefore, the production of 5 liter of red wine led to a grape-pulp waste-stream containing in total 1.780*1.96=3.49 mg cinnamic acid and 1.780*1.94=3.45 mg pinosylvin. Hence, for 1 liter of red wine produced, 3.49/5=0.70 mg of cinnamic acid- and 3.45/5=0.69 mg pinosylvin could be recovered from the pulp waste-stream.

Approximately 20 ml of sediment that was generated in the secondary grape-must fermentation was extracted over-night with 10 ml of ethyl acetate in a 50 ml Sartorious tube, using a rotary unit at ambient temperature (24° C.). The extraction tubes were covered with aluminium foil to avoid any light induced degradation of stilbenoids. The following day the extraction mixture was centrifuged at 3800×g for 10 minutes, and the upper, yellowish/greenish coloured, ethyl acetate was collected and pooled into one tube. From the initial 10 ml of ethyl acetate approximately 8 ml extract was recovered for both the FS1201- and FS9215 sediment suspension. Said ethyl acetate fractions were reduced in volume by evaporation for 2 hours using a freeze dryer until a dry residue was obtained. The dry, dark coloured, residue was dissolved in 500 microliter 50% ethanol which resulted in a solution that contained non-dissolved dark precipitates. The solution was whirly-mixed and centrifuged at 13000×g for 5 minutes and the supernatant was diluted 5-fold with 50% ethanol. Said procedure resulted in a clear yellowish solution that could be used for HPLC analysis.

The sediment of the control strain FS01201 did not contain stilbenoids nor cinnamic- nor coumaric acid (FIG. 8). The chromatogram of the sediment of FS09215 contained a peak with a similar retention time as pinosylvin; indeed said peak with retention time of 4.4 minutes, displayed a UV-spectrum that was identical to pinosylvin (FIGS. 8 and 7). Similarly, the presence of cinnamic acid was confirmed as well. Quantification of the peaks indicated that the sediment contained cinnamic acid and pinosylvin in concentrations of 7.28 mg/l sediment and 2.60 mg/L sediment respectively. The total amount of sediment recovered was approximately 300 ml, and can be considered as secondary waste-stream generated with the production of 5 liter red wine. Therefore, the production of 5 liter of red wine led to a sediment waste-stream containing in total 0.3*7.28=2.18 mg cinnamic acid and 0.3*2.60=0.78 mg pinosylvin. Hence, for 1 liter of red wine produced, 2.18/5=0.44 mg of cinnamic acid- and 0.78/5=0.16 mg of pinosylvin could be recovered from the sediment waste stream.

Hence, for the production of 1 liter of red wine a total waste-stream was produced from which a total amount of 0.70+0.44=1.14 mg cinnamic acid, and 0.69+0.16=0.85 mg pinosylvin could be recovered.

Example 15

Production of Red Wine from Grapes using a *S. cerevisiae* Strain with Constitutive Expression of the Phenylpropanoid Pathway from Tyrosine to Resveratrol.

Commercially available seedless "Crimson" grapes (product of Brazil), are used to produce two red wine's: a control wine produced by using strain FS01201 and a stilbenoid enriched wine by using strain FS-TEF2-TAL-TEF2-4CL-TDH3-VST1 described in example 11. Said strain harbours a phenylpropanoid pathway comprising enzymes that do not use oxygen as substrate. Hence, said strain can produce resveratrol under the oxygen-deprived conditions that typically prevail in the anaerobic fermentation-process used for wine-making.

Preparation of Starter Culture

A starter culture of strain FS01201 and FS-TEF2-TAL-TEF2-4CL-TDH3-VST1 is prepared by crushing 2 kilo's of grapes and filtering the resulting grape pulp with a loose-woven cotton cloth (cheesecloth) and subsequently collecting the grape juice in a sterile open plastic bucket. An aliquot of 500 ml of grape juice is enriched with 40 grams of glucose and divided into two aliquots of 250 ml that are transferred to two sterile 500 ml-shakeflasks. The shakeflasks are inoculated with approximately 2 grams wet-weight of either FS01201 or FS-TEF2-TAL-TEF2-4CL-TDH3-VST1 as prepared according to example 1, and incubated for approximately 24 hours at room temperature. Activity of yeast is indicated by formation of $CO_2$ resulting in a foam-layer.

Primary Pulp Fermentation

A pulp of grapes is prepared by disrupting 16 kilo's of grapes with a semi-professional kitchen blender. The resulting grape-pulp is enriched with approximately 2 coffee-spoons of "yeast nutrient" (stimulates yeast growth) and 3 coffee-spoons of "pecto-enzymes" (breaks down pectin in the grape skin). Both the pecto-enzymes and yeast nutrient are part of a wine-making kit that is commercially available. Said enriched grape-pulp is divided into two equal aliquots, approximately 7 to 8 liter each) and transferred into a 10 liter plastic round sterilized container that is open at the top. A pulp-fermentation is initiated by adding the total amount of 250 ml of starter culture to the grape pulp, and mixing it well together with a large spoon; one bucket is inoculated with FS01201, and the other with FS-TEF2-TAL-TEF2-4CL-TDH3-VST1.

The progression of the pulp-fermentation is visually monitored on a daily basis, and the appearance of a foam-layer on the top, caused by $CO_2$ formation, indicates that the fermentation is successfully ongoing. The $CO_2$ formation causes the grape-pulp to float on top of the grape-juice, and therefore the pulp is mixed with a large spoon on a daily basis as well. The pulp-fermentation is near its end when almost al grape-sugars are consumed, which is indicated by cessation of foam-formation and "fluidizing" of the grape-pulp. The grape pulp is then separated from the liquid fraction (containing the juice and the yeast, i.e. the grape-must) by using a cheesecloth. For each strain approximately 5.0 to 6 liters of grape-must is collected and analyzed for the content of alcohol and stilbenoids. The grape pulp and approximately 1.5 liters of the remaining non-enriched grape-must are stored at 4° C.

Secondary Grape-Must Fermentation

The fermentation is now continued with the grape-must. In order to enhance the alcohol percentage to a level that is usually found in commercial red wines (12- to 15 vol %), an aliquot of 3.5 liter of grape-must of either pulp fermentation is enriched with approximately 340 g of commercially available sugar ("Dansukker", dissolved and heated in approximately 300 ml of water). The addition of the extra sugar causes a dilution of the grape-must, resulting in a slight reduction of ethanol titers. The enriched grape-must is transferred to a 5 liter glass-bottle that is stoppered with a "water-lock" to enable release of $CO_2$, but at the same time preventing contamination. When the ethanol concentration reaches a level in between 12- to 13 vol %., a second sugar-addition is made to enhance the ethanol concentration even further: 150 grams of sugar ("Dansukker") is dissolved into 1400 ml of the previously stored non-enriched grape-must, which is then subsequently added to fermentation glass-bottle. The total volume of the fermentation broth is now approximately 5 liters, and with that almost completely fills the glass bottle leaving no room for air in the top of the bottle. The addition of the extra sugar causes a dilution of the grape-must, resulting in a slight reduction of ethanol titers. The fermentation is finished when all sugars are depleted, and is indicated by a complete cessation of foam formation (i.e. $CO_2$ formation), and the final ethanol concentration is in between 14- to 15 vol %. For each strain the grape-must is analyzed for the content of alcohol and stilbenoids.

In both fermentations sediment settles on the bottom, which likely composes of small-sized particle grape-residues and yeast cells. Said sediment is isolated from the grape-must by siphoning. The sediments are stored at 4° C. until further analysis on stilbenoid content.

Analysis of Waste-Stream for the Presence of Stilbenoids

Approximately 125 grams of the grape pulp that is generated in the primary pulp fermentation is extracted over night with 30 ml of ethyl acetate (divided in three 50 ml Sartorious tubes) using a rotary unit at ambient temperature (24° C.). The extraction tubes are covered with aluminium foil to avoid any light induced degradation of stilbenoids. The following day the extraction mixture is centrifuged at 3800×g for 10 minutes, and the upper, yellow/greenish coloured, ethyl acetate is collected and pooled into one tube. Said ethyl acetate fractions are reduced in volume by evaporation for 2 hours, using a freeze dryer, until a dry residue is obtained. The dry, dark coloured, residue is dissolved in 500 microliter 50% ethanol which results in a solution that contains non-dissolved dark precipitates. The solution is whirly-mixed and centrifuged at 13000×g for 5 minutes and the supernatant is diluted 5-fold with 50% ethanol. Said procedure results in a clear yellowish solution that can be used for HPLC analysis.

The grape-pulp can be considered as a primary waste-stream generated with the production of 5 liter wine, and the resveratrol that can be recovered from the pulp can be expressed in terms of production of 1 liter red-wine.

Approximately 20 ml of sediment that is generated in the secondary grape-must fermentation is extracted over night with 10 ml of ethyl acetate in a 50 ml Sartorious tube, using a rotary unit at ambient temperature (24° C.). The extraction tubes are covered with aluminium foil to avoid any light induced degradation of stilbenoids. The following day the extraction mixture is centrifuged at 3800×g for 10 minutes, and the upper, yellowish/greenish coloured, ethyl acetate is collected and pooled into one tube. Said ethyl acetate fractions are reduced in volume by evaporation for 2 hours, using a freeze-dryer, until a dry residue is obtained. The dry, dark coloured, residue is dissolved in 500 microliter 50% ethanol which results in a solution that contains non-dissolved dark precipitates. The solution is whirly-mixed and centrifuged at 13000×g for 5 minutes and the supernatant is diluted 5-fold with 50% ethanol. Said procedure results in a clear yellowish solution that can be used for HPLC analysis.

The sediment can be considered as a secondary waste-stream generated with the production of 5 liter wine, and resveratrol that can be recovered from the sediment can be expressed in terms of production of 1 liter red-wine.

Hence, for the production of 1 liter of red wine the total amount of resveratrol that can be recovered from the waste-stream can be found by summation of the amount of the resveratrol present in both the primary- and secondary waste-stream.

Example 16

Isolation of Genes Encoding SAM8, 4CL2 and VST1

The codon optimized SAM8 gene encoding *Saccharotrix espaniensis* Tyrosine ammonia lyase (Berner et al, 2006) (SEQ ID NO 38) for expression in *S. cerevisiae* was synthesized by GenScript Corporation (Piscataway, N.J.). The synthetic Sam8 gene was delivered inserted in *E. coli* pUC57 vector flanked by EcoRI and SpeI restriction sites. The synthetic gene was purified from the pUC57 vector by EcoRI/SpeI restriction and purified from agarose gel using the QiaQuick Gel Extraction Kit (Qiagen).

4-coumarate:coenzymeA ligase (4CL2) (Hamberger and Hahlbrock 2004; Ehlting et al., 1999) (SEQ ID NO 39) was isolated via PCR from *A. thaliana* cDNA (BioCat, Heidelberg, Germany) using the primers, Forward 5'GC GAATTCTTATGACGACACAAGATGTGATAGTC AAT-GAT SEQ ID NO 40 with the underlined restriction sequence for ECORI, and Reverse 5'GC ACTAGTATCCTAGTTCATTAATCCATTTGCTAGT CTTGC SEQ ID NO 41 with the underlined restriction site for SpeI.

The codon optimized VST1 gene encoding *Vitis vinifera* (grapevine) resveratrol synthase (Hain et al., 1993) (SEQ ID NO 42) for expression in *S. cerevisiae* was synthesized by GenScript Corporation (Piscataway, N.J.). The synthetic VST1 gene was delivered inserted in *E. coli* pUC57 vector flanked by BamH1 and Xho1 restriction sites. The synthetic gene was purified from the pUC57 vector by BamH1/Xho1 restriction and purified from agarose gel using the QiaQuick Gel Extraction Kit (Qiagen).

Example 17

Construction of a Yeast Vector for Galactose Induced Expression of SAM8

The EcoRI/SpeI digested SAM8 product, isolated as described in example 16, was ligated into EcoRI/SpeI digested pESC-URA vector (Stratagene), resulting in vector pESC-URA-SAM8. Two different clones of pESC-URA-SAM8 were sequenced to verify the sequence of the cloned gene.

Example 18

Construction of a Yeast Vector for Galactose Induced Expression of 4CL2 and VST1

The gene encoding 4CL2 was isolated using the primers as described in example 16. The amplified 4CL2 PCR-product was digested with EcoR1/Spe1 and ligated into EcoR1/Spe1 digested pESC-HIS vector (Stratagene), resulting in vector pESC-HIS-4CL2. Two different clones of pESC-HIS-4CL2 were sequenced to verify the sequence of the cloned gene.

The gene encoding VST1 was isolated as described in example 16. The amplified synthetic VST1 gene was digested with BamH1/Xho1 and ligated into BamH1/Xho1 digested pESC-HIS-4CL2. The resulting plasmid, pESC-HIS-4CL2-VST1, contained the genes encoding 4CL2 and VST1 under the control of the divergent galactose induced <=GAL1/GAL10=> promoters. The sequence of the gene encoding VST1 was verified by sequencing of two different clones of pESC-HIS-4CL2-VST1.

Example 19

Construction of Strong Constitutive Promoter Fragment TDH3

The 600 base pair TDH3 (GPD) promoter was amplified from S. cerevisiae genomic DNA using the forward primer 5'GC GAGCTC AGT TTA TCA TTA TCA ATA CTC GCC ATT TCA AAG SEQ ID NO 43 containing a Sac1 restriction site and the reverse primer 5'-CG TCTAGA ATC CGT CGA AAC TAA GTT CTG GTG TTT TAA AAC TAA AA SEQ ID NO 44 containing a Xba1 restriction site. The amplified TDH3 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TDH3.

Example 20

Construction of Constitutive Strong Promoter Fragment TEF2

The 400 base pair TEF2 promoter was amplified from S. cerevisiae genomic DNA using the forward primer 5'-GC GAGCTC ATA GCT TCA AAA TGT TTC TAC TCC TTT TTT ACT CTT SEQ ID NO 45 containing a Sac1 restriction site and the reverse primer 5'-CG TCTAGA AAA CTT AGA TTA GAT TGC TAT GCT TTC TTT CTA ATG A SEQ ID NO 46 containing a Xba1 restriction site. The amplified TEF2 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TEF2.

Example 21

Construction of Fused Divergent Constitutive TEF and TDH3 Promoter Fragment

A divergent fusion fragment between TEF2 promoter and TDH3 promoter was constructed starting from PRS416-TEF and PRS416-TDH3.

The 600 base pair TDH3 fragment was reamplified from PRS416-TDH3 using the forward primer 5' TTGCGTATTGGGCGCTCTTCC GAG CTC AGT TTA TCA TTA TCA ATA CTC GC SEQ ID NO 47 containing the underlined overhang for fusion PCR to TEF2 fragment and the reverse primer 5' AT GGATCC TCT AGA ATC CGT CGA AAC TAA GTT CTG SEQ ID NO 48 containing the underlined BamH1 restriction site. This resulted in a fragment ready for fusion to the below TEF2 fragment.

The 400 base pair TEF2 fragment including a 277 base pair spacer upstream of the Sac1 restriction site was reamplified from PRS416-TEF2 using the forward primer 5' AT GAATTC TCT AGA AAA CTT AGA TTA GAT TGC TAT GCT TTC SEQ ID NO 49 containing the underlined EcoR1 restriction site and the reverse primer 5' TGATAATGATAAACTGAGCTC GGA AGA GCG CCC AAT ACG CAA AC SEQ ID NO 50 containing the underlined overhang for fusion to the TDH3 fragment. This resulted in a 680 base pair fragment ready for fusion to the TDH3 fragment. The 680 base pair TEF2 fragment and the 600 base pair TDH3 fragments were joined together (fused) using fusion PCR with the forward primer 5' AT GAATTC TCT AGA AAA CTT AGA TTA GAT TGC TAT GCT TTC SEQ ID NO 51 and the reverse primer 5' AT GGATCC TCT AGA ATC CGT CGA AAC TAA GTT CTG SEQ ID NO 52, resulting in the divergent fragment <=TEF2/TDH3=> (SEQ ID NO 53).

Example 22

Construction of a Yeast Vector for Constitutive Expression of Sam8

The vector pESC-URA-Sam8 with divergent galactose inducible promoters GAL1/GAL10 was sequentially digested with EcoRI and BamHI to remove the GAL1/GAL10 promoters.

The divergent constitutive <=TEF2/TDH3=> promoter fragment (Example 21) was re-amplified with forward primer 5' AT GGATCC TCT AGA AAA CTT AGA TTA GAT TGC TAT GCT TTC SEQ ID NO 54 and reverse primer 5'AT GAATTC TCTAGA ATC CGT CGAAACTAAGTTCTGG SEQ ID NO 55.

The resulting PCR product was sequentially digested with ECORI and BamH1 and ligated into the above ECORI/BamHI digested vector (pESC-URA-Sam8) without the GAL1/Gal10 fragment. This resulted in a vector pESC-URA-TDH3-Sam8 with replaced promoters, from GAL1/Gal10 to TEF2/TDH3 (SEQ ID NO 56).

Example 23

Construction of a Yeast Vector for Constitutive Expression Induced of 4CL2 and VST1

The vector pESC-HIS-4CL2-VST1 with divergent galactose inducible promoters GAL1/GAL10 was sequentially digested with EcoR1 and BamH1 to remove the GAL1/GAL10 promoters.

The divergent constitutive <=TEF2/TDH3=> promoter fragment (Example 21) was sequentially digested with EcoR1 and BamH1 and ligated into the above linearized vector without the GAL1/GAL10 fragment. This resulted in a vector pesc-HIS-TEF2-4CL2-TDH3-VST1 with replaced promoters, from GAL1/Gal10 to TEF2/TDH3 (SEQ ID NO 57).

Example 24

Generation of Strain with Constitutive Expression of the Pathway to Resveratrol in the Yeast *S. cerevisiae*.

The transformation of the yeast cell was conducted in accordance with methods known in the art, for instance by using lithium acetate transformation method (Gietz and Schiestl, 1991). *S. cerevisiae* strain FS01528 (CEN.PK MATa ura3 His3) was co-transformed with pESC-URA-TDH3-SaM8 (example 22) and pesc-HIS-TEF2-4CL2-TDH3-VST1 (example 23), and the transformed strain was named FS-SAM8-4CL2-VST1. Transformants were selected on medium lacking uracil and histidine and streak purified on the same medium.

Example 25

Generation of Biomass

Batch fermentation of FS-SAM8-4CL2-VST1 were carried out in order to generate wet biomass for inoculation of the wine fermentation. The fermentation was carried out in a Sartorius Biostat B plus fermentor under aerobic conditions. The working volume was 1 L, agitation was 1000 rpm, and air flow was set to 1.5 vvm. Temperature and pH were 30° C. and 5.5, respectively. The fermentation was inoculated to an initial OD of 0.0005. The composition is described in the following:

Media:

| Compound Concentration | [g/L] |
|---|---|
| Glucose | 165 |
| Urea | 22.72 |
| KH2PO4 | 30 |
| MgSO4 | 5 |
| Vitamin solution | 10 mL* |
| Trace metal solution | 10 mL* |
| Antifoam | 100 µL |

Vitamin Solution

| Concentration | [g/L] |
|---|---|
| Biotin | 0.05 |
| Calcium panthotenate | 1 |
| Nicotinic acid | 1 |
| Myo-inositol | 25 |
| Thiamine HCl | 1 |
| Pyridoxal HCl | 1 |
| Para-aminobenzoic acid | 0.2 |

Trace Metal Solution

| Concentration | [g/L] |
|---|---|
| EDTA | 15 |
| ZnSO4x7H2O | 4.5 |
| MnCl2x2H2O | 1 |
| CoCl2x6H2O | 0.3 |
| CuSO4x5H2O | 0.3 |
| Na2MoO4x2H2O | 0.4 |
| CaCl2x2H2O | 4.5 |
| FeSO4x7H2O | 3 |
| H3BO3 | 1 |
| KI | 0.1 |

At the end of the fermentation, when all glucose was depleted, the biomass was harvested into Falcon tubes by centrifugation. Four 50 mL sterile Falcon tubes were used and the cells were harvested using 5 consecutive centrifuge runs at 4° c. with 4000 rpm for five minutes. The centrifuge used was a Satorius Sigma 3-16K including a swing out rotor with for buckets. The supernatant was each discarded after each run. The four tubes contained approximately 70 g of wet biomass, which was used as inoculum for the wine fermentation.

Example 26

Resveratrol Production by Fermenting Wine

Objective: To evaluate the relative efficacy of producing resveratrol by wine fermentation using wine juice concentrate as plant material compared to commercially available wine yeast, Two identical wine making kits procured from Winexpert Incorporated of Canada were used as the basis of making a comparison between the commercially available yeast *Saccharomyces bayanus* (Lalvin EC1118), the control strain, for wine making versus FS-SAM8-4CL2-VST1. The kit used was the "Selection Original—Barolo Style." This style utilizes the Nebbiolo red grape as the basis of the grape juice concentrate. This concentrate is preserved with suphur dioxide, citric acid, malic acid, tartaric acid, and diammonium phosphate. Also supplied in the kit are single packages of a premeasured amount of bentonite for use as a clarifying agent, potassium metabisuphite as a stabilizer, and oak chips used for flavoring. The package of oak chips was not used in this experiment for either fermentation. Kit designated Lot 07318080147 was used for fermentation of *Saccharomyces bayanus* (Lalvin EC1118) and Lot 07318080172 was for fermentation of FS-SAM8-4CL2-VST1.

Each of two kits was treated similarly except for the inoculum. For the wine fermentation using the control strain five grams of yeast (Lalvin EC1118 of Lallemand Inc.) were used, whereas for FS-SAM8-4CL2-VST1 18 g of wet biomass, which was approximately 5 g/L dry weight, was used as inoculum.

Before inoculation, all equipment and containers being used were first sanitized with a solution of metabisulfite (~50 grams in 4 liters). Spring water ("Deerpark") was used for all solutions. Two liters of warm water (~300° C.) were added to a clean 30 liter plastic carboy container and stirred vigorously while slowly sprinkling in the contents of the bentonite package until fully wetted and dispersed; for approximately one minute. The grape juice concentrate (15 L) were filled into the containers. The package of grape juice concentrate was washed with 4 liters, which was afterwards added to container. The final container volume was adjusted to 23 liters with cool. The oak chip package intended to be used as a flavoring enhancer was not used in either the control or treatment groups. With the juice solution at about room temperature (~20.0° C.), the package of Lalvin yeast was sprinkled on top of the control juice solution and FS-SAM8-4CL2-VST1 was poured into solution. Each container (primary fermentor) was covered with an air-lock. The wine was fermented for 50 days. Samples of wine and mash were taken at the end of the fermentation and placed into a sealed plastic cup and stored frozen until analyses.

Example 27

Extraction of Resveratrol from Wine-Mash

Two duplicate samples of the mash from the control- and treatment groups were evaluated for their content of stilbenoids, hereafter referred to as control A, control B, treatment A and treatment B. Aliquots of 50 ml of either samples, containing a mixture of mash and wine, were centrifuged for 10 minutes at 3500×G at 10° C., after which the supernatant was discarded. Hereafter, the wet weight content of mash was 12.57 g for control A, 14.03 g for control B, 11.63 g for treatment A and 12.52 g for treatment B. Next, 10 ml of 99% ethyl acetate was added and whirly-mixed at room temperature on an automated whirly mixer for 2 hours at 2500 rpm. Then samples were centrifuged for 10 minutes at 3500×g at 10° C., and the upper, yellow/reddish coloured, ethyl acetate was collected reduced in volume by evaporation in a freeze-dryer. After approximately 2 hours a dry reddish residue was obtained, which was carefully resuspended in 120 µl 20% ethanol and resulted in a solution that contained non-dissolved dark precipitates. The solution was, therefore, whirly-mixed and centrifuged at 13000×g for 5 minutes. The supernatant now consisted of a clear reddish 20%-ethanol solution, which was diluted 100-fold further in two steps of 10-fold; the first dilution step was rendered in 20%-ethanol whereas Millipore water was used for the subsequent second 10-fold dilution step. Samples were then ready to be analyzed by HPLC.

Example 28

HPLC Determination of Stilbenoids and Phenylpropanoids

For quantitative analysis of coumaric acid, cinnamic acid, trans-resveratrol and trans-pinosylvin, samples were subjected to separation by high-performance liquid chromatography (HPLC), using a HPLC-system from Dionex, prior to UV-diode-array detection at l=306 nm. A Phenomenex (Torrance, Calif., USA) Gemini C6-Phenyl, 3 micron (100×3.00 mm) column was used at 35° C. The method consisted of a linear gradient of methanol and millipore water (both containing 50 ppm trifluoroacetic acid), at a flow rate of 0.5 ml/min. The gradient profile was linear from 20% methanol to 100% methanol over 20 min. The elution times were 7.5 min. for coumaric acid, 10.1 min. for trans-resveratrol, 11.8 min. for cinnamic acid and 14.0 min for pinosylvin.

Example 29

Concentration of Resveratrol in the Mash

The chromatograms of both the control group and the treatment group contained all a peak with a similar retention time as resveratrol (9.9 minutes) and with an UV spectrum that resembled the UV spectrum of resveratrol. Quantification of the peak indicated that the resveratrol content in the mash was 0.33 mg/kg for control A, 0.48 mg/kg for control B, giving an average of 0.41 mg/kg for the control group. The mash of treatment A contained 0.80 mg/kg and treatment B contained 0.73 mg/kg, giving an average resveratrol content of 0.77 mg/kg for the treatment group. Hence, on average, the mash of the treatment group contained 89% more resveratrol than the mash of the control group.

It can, therefore, be concluded that the use of resveratrol-producing yeast in a wine fermentation process has led to a substantial enrichment of the resveratrol in the mash.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

Becker et al, Ferns Yeast Research, 4, 2003, 79-85 Metabolic engineering of *Saccharomyces cerevisiae* for the synthesis of the wine related antioxidant resveratrol Berner M, Krug D, Bihlmaier C, Vente A, Müller R, Bechthold A. Genes and enzymes involved in caffeic acid biosynthesis in the actinomycete *Saccharothrix espanaensis*. J Bacteriol. 2006:188:2666-73

Cochrane F C, Davin L B, Lewis N G. The *Arabidopsis* phenylalanine ammonia lyase gene family: kinetic characterization of the four PAL isoforms. Phytochemistry. 2004: 65:1557-64.

Ehlting J, Büttner D, Wang Q, Douglas C J, Somssich I E, Kombrink E. Three 4-coumarate:coenzyme A ligases in *Arabidopsis thaliana* represent two evolutionarily divergent classes in angiosperms. Plant J. 1999:19:9-20.

Hain R, Reif H J, Krause E, Langebartels R, Kindl H, Vornam B, Wiese W, Schmelzer E, Schreier P H, Stocker R H, et al. Disease resistance results from foreign phytoalexin expression in a novel plant. Nature. 1993:361:153-6.

Hamberger B, Hahlbrock K. The 4-coumarate:CoA ligase gene family in *Arabidopsis thaliana* comprises one rare, sinapate-activating and three commonly occurring isoenzymes. Proc Natl Acad Sci USA. 2004:101:2209-14.

Gietz R D, Schiestl R H. Applications of high efficiency lithium acetate transformation of intact yeast cells using single-stranded nucleic acids as carrier. Yeast. 1991:7:253-63.

Mizutani M, Ohta D, Sato R. Isolation of a cDNA and a genomic clone encoding cinnamate 4-hydroxylase from Arabidopsis and its expression manner in planta. Plant Physiol. 1997:113:755-63.

Mizutani M, Ohta D. Two isoforms of NADPH:cytochrome P450 reductase in *Arabidopsis thaliana*. Gene structure, heterologous expression in insect cells, and differential regulation. Plant Physiol. 1998:116:357-67.

Mumberg D, Müller R, Funk M. Yeast vectors for the controlled expression of heterologous proteins in different genetic backgrounds. Gene. 1995:156:119-22.

Sikorski R S, Hieter P. A system of shuttle vectors and yeast host strains designed for efficient manipulation of DNA in *Saccharomyces cerevisiae*. Genetics. 1989:122:19-27.

Verduyn C, Postma E, Scheffers W A, Van Dijken J P. Effect of benzoic acid on metabolic fluxes in yeasts: a continuous-culture study on the regulation of respiration and alcoholic fermentation. Yeast. 1992:8:501-17.

The invention claimed is:

1. A method for the production of a mixture comprising stilbenoids, comprising extracting resveratrol or pinosylvin from a solids waste material separated from a fermentation of plant material conducted using a genetically modified yeast strain having a metabolic pathway producing the mixture comprising stilbenoids, wherein the genetically modified yeast is a yeast strain comprising a vector comprising SEQ ID NO:56.

2. The method of claim 1, further comprising the preliminary steps of conducting said fermentation of plant material using the genetically modified yeast having a metabolic pathway producing the mixture comprising stilbenoids and separating a solids waste material from said fermentation.

3. The method of claim 1, wherein the fermentation is a fermentation of fruit must together with or separated from pommace.

4. The method of claim 1, wherein the fermentation is a fermentation of pommace separated from fruit must.

5. The method of claim 2, wherein the fruit is grape, apple or pear.

6. The method of claim 1, wherein the fermentation is a beer making fermentation.

7. The method of claim 1, wherein the genetically modified yeast is from the *Saccharomyces* genus.

8. The method of claim 1, further comprising the step of recovering resveratrol or pinosylvin.

9. The method of claim 1, wherein the genetically modified yeast strain further comprises a vector comprising SEQ ID NO: 57.

* * * * *

SEQUENCE LISTING

<160> NUMBER OF SEQ ID NOS: 57

<210> SEQ ID NO 1
<211> LENGTH: 2154
<212> TYPE: DNA
<213> ORGANISM: Arabidopsis thaliana

<400> SEQUENCE: 1

```
atggatcaaa tcgaagcaat gttgtgcggc ggaggagaga agacaaaagt ggcggttact      60
acgaagactt tggcagatcc attgaattgg ggtttagcag cggatcaaat gaaaggaagt     120
catttagatg aagtgaagaa gatggtcgaa gagtatcgta gaccagtcgt gaatcttggc     180
ggagaaacac tgacgatcgg acaagttgct gccatctcca ccgtaggagg cagcgttaag     240
gttgagttag cggagacttc aagagccggt gtgaaagcta gcagtgattg ggttatggag     300
agcatgaaca aggtactgac agttacggag tcaccaccgc tctttggtgc tacttctcac     360
cggagaacca aaaacggcac cgcattacaa acagaactca ttagattttt gaacgccgga     420
atattcggaa acacgaagga gacatgtcac acactgccgc aatccgccac aagagccgcc     480
atgctcgtca gagtcaacac tcttctccaa ggatactccg ggatccgatt cgagatcctc     540
gaagcgatta caagtctcct caaccacaac atctctccgt cactacctct ccgtggaacc     600
attaccgcct ccggcgatct cgttcctctc tcttacatcg ccggacttct caccggccgt     660
cctaattcca aagccaccgg tcccgacggt gaatcgctaa ccgcgaaaga agcttttgag     720
aaagccggaa tcagtactgg attcttcgat ttacaaccta aggaaggttt agctctcgtt     780
aatggcacgg cggttggatc tggaatggcg tcgatggttc tattcgaagc gaatgtccaa     840
gcggtgttag cggaggtttt atcagcgatc ttcgcggagg ttatgagcgg gaaacctgag     900
tttaccgatc atctgactca tcgtttaaaa catcatcccg gacaaatcga agcggcggcg     960
ataatggagc acatactcga cggaagctca tacatgaaat agctcaaaa ggttcacgag    1020
atggatccat gcagaaacc aaaacaagat cgttacgctc ttcgtacatc tcctcaatgg    1080
ctaggtcctc aaattgaagt aatccgtcaa gctacgaaat cgatagagcg tgaaatcaac    1140
tccgttaacg ataatccgtt gatcgatgtt tcgaggaaca aggcgattca cggtggtaac    1200
ttccaaggaa caccaatcgg agtttctatg gataacacga gattggcgat gctgcgatt     1260
gggaagctaa tgtttgctca attctctgag cttgttaatg atttctacaa caatggactt    1320
ccttcgaatc taactgcttc gagtaatcca agtttggatt atggattcaa aggagcagag    1380
attgctatgg cttcttattg ttctgagctt caatacttgg ctaatccagt cacaagccat    1440
gttcaatcag ctgagcaaca taatcaagat gtgaactctc ttggtttgat ctcgtctcgt    1500
aaaacatctg aagctgtgga tattcttaag ctaatgtcaa caacgttcct tgtggggata    1560
tgtcaagctg ttgatttgag acatttggag gagaatctga caaactgt gaagaacaca     1620
gtttctcaag ttgctaagaa agtgttaacc actggaatca acggtgagtt acatccgtca    1680
aggttttgcg agaaggactt gcttaaggtt gttgatcgtg agcaagtgtt cacgtatgtg    1740
gatgatcctt gtagcgctac gtacccgttg atgcagagac taagacaagt tattgttgat    1800
cacgcttttgt ccaacggtga gactgagaag aatgcagtga cttcgatctt tcaaaagatt    1860
ggagcttttg aagaggagct taaggctgtg cttccaaagg aagttgaagc ggctagagcg    1920
gcttatggga tggaactgc gccgattcct aaccggatta ggaatgtag gtcgtatccg     1980
ttgtataggt tcgtgaggga agagcttgga acgaagttgt tgactggaga aaaggttgtg    2040
```

| | |
|---|---|
| tctccgggag aggagtttga taaggtcttc actgctatgt gtgaaggtaa acttattgat | 2100 |
| ccgttgatgg attgtctcaa ggaatggaac ggagctccga ttccgatttg ctaa | 2154 |

<210> SEQ ID NO 2
<211> LENGTH: 1518
<212> TYPE: DNA
<213> ORGANISM: Arabidopsis thaliana

<400> SEQUENCE: 2

| | |
|---|---|
| atggacctcc tcttgctgga gaagtcttta atcgccgtct tcgtggcggt gattctcgcc | 60 |
| acggtgattt caaagctccg cggcaagaaa ttgaagctac ctccaggtcc tataccaatt | 120 |
| ccgatcttcg gaaactggct tcaagtcgga gatgatctca accaccgtaa tctcgtcgat | 180 |
| tacgctaaga attcggcga tctcttcctc ctccgtatgg gtcagcgaaa cctagtcgtc | 240 |
| gtctcctcac cggatctaac aaaggaagtg ctcctcactc aaggcgttga gtttggatcc | 300 |
| agaacgagaa acgtcgtgtt cgacattttc accgggaaag gtcaagatat ggtgttcact | 360 |
| gtttacggcg agcattggag gaagatgaga agaatcatga cggttccttt cttcaccaac | 420 |
| aaagttgttc aacagaatcg tgaaggttgg gagtttgaag cagctagtgt tgttgaagat | 480 |
| gttaagaaga atccagattc tgctacgaaa ggaatcgtgt tgaggaaacg tttgcaattg | 540 |
| atgatgtata caatatgtt ccgtatcatg ttcgatagaa gatttgagag tgaggatgat | 600 |
| cctctttttcc ttaggcttaa ggctttgaat ggtgagagaa gtcgattagc tcagagcttt | 660 |
| gagtataact atgagatttt cattcctatc cttagaccat tcctcagagg ctatttgaag | 720 |
| atttgtcaag atgtgaaaga tcgaagaatc gctcttttca agaagtactt tgttgatgag | 780 |
| aggaagcaaa ttgcgagttc taagcctaca ggtagtgaag gattgaaatg tgccattgat | 840 |
| cacatccttg aagctgagca gaaggagaa atcaacgagg acaatgttct ttacatcgtc | 900 |
| gagaacatca atgtcgccgc gattgagaca acattgtggt ctatcgagtg ggaattgca | 960 |
| gagctagtga accatcctga aatccagagt aagctaagga acgaactcga cacagttctt | 1020 |
| ggaccgggtg tgcaagtcac cgagcctgat cttcacaaac ttccatacct tcaagctgtg | 1080 |
| gttaaggaga ctcttcgtct gagaatggcg attcctctcc tcgtgcctca catgaacctc | 1140 |
| catgatgcga agctcgctgg ctacgatatc ccagcagaaa gcaaaatcct tgttaatgct | 1200 |
| tggtggctag caaacaaccc caacagctgg aagaagcctg aagagtttag accagagagg | 1260 |
| ttctttgaag aagaatcgca cgtggaagct aacggtaatg acttcaggta tgtgccattt | 1320 |
| ggtgttggac gtcgaagctg tccccgggatt atattggcat tgcctattt ggggatcacc | 1380 |
| attggtagga tggtccagaa cttcgagctt cttcctcctc caggacagtc taaagtggat | 1440 |
| actagtgaga aggtggaca attcagcttg cacatcctta accactccat aatcgttatg | 1500 |
| aaaccaagga actgttaa | 1518 |

<210> SEQ ID NO 3
<211> LENGTH: 2136
<212> TYPE: DNA
<213> ORGANISM: Arabidopsis thaliana

<400> SEQUENCE: 3

| | |
|---|---|
| atgtcctctt cttcttcttc gtcaacctcc atgatcgatc tcatggcagc aatcatcaaa | 60 |
| ggagagcctg taattgtctc cgacccagct aatgcctccg cttacgagtc cgtagctgct | 120 |
| gaattatcct ctatgcttat agagaatcgt caattcgcca tgattgttac cacttccatt | 180 |
| gctgttctta ttggttgcat cgttatgctc gtttggagga gatccggttc tgggaattca | 240 |

```
aaacgtgtcg agcctcttaa gcctttggtt attaagcctc gtgaggaaga gattgatgat    300
gggcgtaaga aagttaccat cttttcggt acacaaactg gtactgctga aggttttgca    360
aaggctttag gagaagaagc taaagcaaga tatgaaaaga ccagattcaa atcgttgat     420 ttggatgatt acgcggctga tgatgatgag tatgaggaga aattgaagaa agaggatgtg    480
gctttcttct tcttagccac atatggagat ggtgagccta ccgacaatgc agcgagattc    540
tacaaatggt tcaccgaggg gaatgacaga ggagaatggc ttaagaactt gaagtatgga    600
gtgtttggat taggaaacag acaatatgag cattttaata aggttgccaa agttgtagat    660
gacattcttg tcgaacaagg tgcacagcgt cttgtacaag ttggtcttgg agatgatgac    720
cagtgtattg aagatgactt taccgcttgg cgagaagcat tgtggcccga gcttgataca    780
atactgaggg aagaagggga tacagctgtt gccacaccat acactgcagc tgtgttagaa    840
tacagagttt ctattcacga ctctgaagat gccaaattca atgatataaa catggcaaat    900
gggaatggtt acactgtgtt tgatgctcaa catccttaca agcaaatgt cgctgttaaa     960 agggagcttc atactcccga gtctgatcgt tcttgtatcc atttggaatt tgacattgct    1020
ggaagtggac ttacgtatga aactggagat catgttggtg tactttgtga taacttaagt    1080
gaaactgtag atgaagctct tagattgctg gatatgtcac ctgatactta tttctcactt    1140
cacgctgaaa agaagacgg cacaccaatc agcagctcac tgcctcctcc cttcccacct    1200
tgcaacttga acagcgct tacacgatat gcatgtcttt tgagttctcc aaagaagtct     1260
gctttagttg cgttggctgc tcatgcatct gatcctaccg aagcagaacg attaaaacac    1320
cttgcttcac ctgctggaaa ggatgaatat tcaaagtggg tagtagagag tcaaagaagt    1380
ctacttgagg tgatggccga gtttccttca gccaagccac cacttggtgt cttcttcgct    1440
ggagttgctc aaggttgca gcctaggttc tattcgatat catcatcgcc caagattgct     1500
gaaactagaa ttcacgtcac atgtgcactg gtttatgaga aaatgccaac tgcaggatt     1560 cataagggag tgtgttccac ttggatgaag aatgctgtgc cttacgagaa gagtgaaaac    1620
tgttcctcgg cgccgatatt tgttaggcaa tccaacttca agcttccttc tgattctaag    1680
gtaccgatca tcatgatcgg tccagggact ggattagctc cattcagagg attccttcag    1740
gaaagactag cgttggtaga atctggtgtt gaacttgggc catcagtttt gttctttgga    1800
tgcagaaacc gtagaatgga tttcatctac gaggaagagc tccagcgatt tgttgagagt    1860
ggtgctctcg cagagctaag tgtcgccttc tctcgtgaag acccaccaa agaatacgta    1920 cagcacaaga tgatggacaa ggcttctgat atctggaata tgatctctca aggagcttat    1980
ttatatgttt gtggtgacgc caaaggcatg gcaagagatg ttcacagatc tctccacaca    2040
atagctcaag aacaggggtc aatggattca actaaagcag agggcttcgt gaagaatctg    2100
caaacgagtg aagatatctc tagagatgta tggtaa                              2136
```

<210> SEQ ID NO 4
<211> LENGTH: 1686
<212> TYPE: DNA
<213> ORGANISM: Arabidopsis thaliana

<400> SEQUENCE: 4

```
atggcgccac aagaacaagc agtttctcag gtgatggaga acagagcaa caacaacaac      60 agtgacgtca ttttccgatc aaagttaccg gatatttaca tcccgaacca cctatctctc    120
cacgactaca tcttccaaaa catctccgaa ttcgccacta gccttgcct aatcaacgga    180 ccaaccggcc acgtgtacac ttactccgac gtccacgtca tctcccgcca aatcgccgcc    240
```

-continued

| | |
|---|---|
| aattttcaca aactcggcgt taaccaaaac gacgtcgtca tgctcctcct cccaaactgt | 300 |
| cccgaattcg tcctctcttt cctcgccgcc tccttccgcg gcgcaaccgc caccgccgca | 360 |
| aacccttct tcactccggc ggagatagct aaacaagcca aagcctccaa caccaaactc | 420 |
| ataatcaccg aagctcgtta cgtcgacaaa atcaaaccac ttcaaaacga cgacggagta | 480 |
| gtcatcgtct gcatcgacga caacgaatcc gtgccaatcc ctgaaggctg cctccgcttc | 540 |
| accgagttga ctcagtcgac aaccgaggca tcagaagtca tcgactcggt ggagatttca | 600 |
| ccggacgacg tggtggcact accttactcc tctggcacga cgggattacc aaaaggagtg | 660 |
| atgctgactc acaagggact agtcacgagc gttgctcagc aagtcgacgg cgagaacccg | 720 |
| aatctttatt tccacagcga tgacgtcata ctctgtgttt tgcccatgtt tcatatctac | 780 |
| gctttgaact cgatcatgtt gtgtggtctt agagttggtg cggcgattct gataatgccg | 840 |
| aagtttgaga tcaatctgct attggagctg atccagaggt gtaaagtgac ggtggctccg | 900 |
| atggttccgc cgattgtgtt ggccattgcg aagtcttcgg agacggagaa gtatgatttg | 960 |
| agctcgataa gagtggtgaa atctggtgct gctcctcttg gtaaagaact tgaagatgcc | 1020 |
| gttaatgcca agtttcctaa tgccaaactc ggtcagggat acggaatgac ggaagcaggt | 1080 |
| ccagtgctag caatgtcgtt aggttttgca aaggaaccct ttccggttaa gtcaggagct | 1140 |
| tgtggtactg ttgtaagaaa tgctgagatg aaaatagttg atccagacac cggagattct | 1200 |
| ctttcgagga atcaacccgg tgagatttgt attcgtggtc accagatcat gaaaggttac | 1260 |
| ctcaacaatc cggcagctac agcagagacc attgataaag acggttggct tcatactgga | 1320 |
| gatattggat tgatcgatga cgatgacgag cttttcatcg ttgatcgatt gaaagaactt | 1380 |
| atcaagtata aggttttca ggtagctccg gctgagctag aggctttgct catcggtcat | 1440 |
| cctgacatta ctgatgttgc tgttgtcgca atgaaagaag aagcagctgg tgaagttcct | 1500 |
| gttgcatttg tggtgaaatc gaaggattcg gagttatcag aagatgatgt gaagcaattc | 1560 |
| gtgtcgaaac aggttgtgtt ttacaagaga atcaacaaag tgttcttcac tgaatccatt | 1620 |
| cctaaagctc catcagggaa gatattgagg aaagatctga gggcaaaact agcaaatgga | 1680 |
| ttgtga | 1686 |

<210> SEQ ID NO 5
<211> LENGTH: 1182
<212> TYPE: DNA
<213> ORGANISM: Vitis vinifera

<400> SEQUENCE: 5

| | |
|---|---|
| atggcatccg tagaggagtt cagaaatgca cagagggcaa aagtccagc aaccatattg | 60 |
| gctattggaa cagccacccc tgatcactgt gtttatcaat ctgattacgc tgattactat | 120 |
| ttcagagtaa ctaaaagtga acatatgaca gaacttaaga aaaagtttaa tagaatttgt | 180 |
| gataaatcta tgataaagaa aagatacata catctaactg aagaaatgtt agaggaacat | 240 |
| ccaaatatag gtgcatatat ggcaccatct ttgaatatta gacaagaaat cataacagcc | 300 |
| gaggtaccta actaggtag agacgcagcc ttgaaagctt taaaggaatg ggacaaccca | 360 |
| aaatctaaga ttacacattt ggttttctgt acaacttccg gtgtcgaaat gccaggtgct | 420 |
| gattataaac tagcaaacct attgggatta gagacctctg ttagaagagt tatgttgtat | 480 |
| catcaaggtt gttacgccgg aggtacagtg cttagaactg ctaaggattt ggcagaaaat | 540 |
| aacgccggtg ctagggtttt agtcgtctgc agtgaaatca ctgtcgtaac ttcagaggt | 600 |
| ccatcagaag atgctctaga cagtttggtc ggacaagcat tgtttggcga tggatcttcc | 660 |

```
gccgtaattg taggcagcga tcctgatgtg tccattgaaa gaccactatt tcaattagtt      720
tctgctgctc aaacttttat tccaaattcc gccggtgcca tagcaggaaa cttgagagaa      780
gttggtttga cttttcattt gtggcctaat gtcccaacct taatttcaga aaacatcgaa      840
aaatgcttaa ctcaagcctt tgacccattg gcataagcg actggaactc attgttttgg       900
attgctcatc caggtggtcc agcaatttta dacgcagtgg aggcaaaact aaacttagag      960
aagaaaaagt tggaagctac aagacacgtt ctatcagagt atggcaacat gagctctgcc     1020
tgcgttttat tcattctaga tgagatgagg aagaagtctt taagggtga aaaagccaca      1080 accggagaag gtttagattg gggtgttcta tttggtttcg gtcctggctt aacaattgag     1140
acagtggtgt tacactctgt tccaactgtc actaactaat ga                        1182

<210> SEQ ID NO 6
<211> LENGTH: 1596
<212> TYPE: DNA
<213> ORGANISM: Rhodobacter capsulatus

<400> SEQUENCE: 6
atgaccctgc aatctcaaac agctaaagat tgtttggctt tggatggtgc cttgacatta      60
gttcaatgcg aagcgatagc aacccataga agtagaatct ctgtaacacc agccctacgt     120
gagagatgtg ctagagcaca tgctaggtta gaacatgcaa tagccgaaca gcgacacata     180
tatgggataa cgacaggctt cgggccactt gctaacaggc tgatcggagc agaccagggt     240
gctgaattac aacagaacct tatctaccat ttggcaaccg gagttggccc caaattatca     300
tgggccgaag ccagagcttt aatgctcgct cgtttgaata gtatactaca aggtgcttct     360
ggtgctagcc ctgaaacaat tgataggatc gttgcagtct taaatgccgg atttgccccg     420
gaagtcccag cccaaggaac cgttggtgct tcgggtgact taactccgtt agcacacatg     480
gtattagcat tgcaaggcag aggtcgtatg attgatcctt cagggagagt tcaagaagcc     540
ggcgctgtca tggataggtt gtgtggaggc cctttaacat tggctgccag agatggcctc     600
gccttagtaa atggtacatc tgccatgaca gctattgccg cattgaccgg tgtggaggct     660
gcaagagcga ttgatgcagc gcttagacat tccgcagtct tgatggaggt cctgtcaggg     720
catgctgagg cttggcaccc tgcctttgcg gaattgcgtc cgcatccagg acaattacgc     780
gccactgaga ggttagctca agcattggac ggcgcaggta gagtctgccg gactcttaca     840
gccgctaggc gtctaactgc agctgatctg agaccagaag atcatccagc tcaagatgca     900
tattcacttc gagtagttcc tcagctggtt ggtgccgtat gggatacgtt ggattggcac     960
gacagggttg tgacttgcga acttaactcc gtgaccgaca atccaatttt ccccgagggt    1020
tgtgcggttc cagcactaca cggtggaaac tttatgggcg tacatgtggc actagcttct    1080
gacgctttaa atgcagcgtt ggttacatta gctggtctag ttgaaaggca gattgcaaga    1140
cttactgatg agaagttgaa taagggtttg cctgcttttt tgcatggagg ccaagcaggt    1200
ttacaatcag gtttcatggg agctcaggtt actgctactg ctttgctagc ggaaatgaga    1260
gctaacgcga ctcccgtgtc cgttcaaagc ctcagcacca atggtgcaaa tcaagacgtg    1320
gtaagtatgg gtacgattgc cgcgagacga gcaagagctc aacttttacc tctgtctcaa    1380
atccaagcga ttttggcact ggctcttgca caagccatgg atctcctaga cgatcctgaa    1440
ggacaagccg gttggtcctt aacggcaaga gatttaagag accgtatacg ggctgtcagt    1500
ccagggttgc gcgcagatag accactagcg ggtcatattg aagctgtggc tcaaggtcta    1560
agacacccct cggcagctgc cgatccacct gcttaa                              1596
```

<210> SEQ ID NO 7
<211> LENGTH: 1373
<212> TYPE: DNA
<213> ORGANISM: artificial
<220> FEATURE:
<223> OTHER INFORMATION: TEF2 fragment fused to TDH3 fragment

<400> SEQUENCE: 7

| | | | | | |
|---|---|---|---|---|---|
| atgaattctc | tagaaaactt | agattagatt | gctatgcttt | ctttctaatg | agcaagaagt | 60 |
| aaaaaaagtt | gtaatagaac | aagaaaaatg | aaactgaaac | ttgagaaatt | gaagaccgtt | 120 |
| tattaactta | aatatcaatg | ggaggtcatc | gaaagagaaa | aaaatcaaaa | aaaaaatttt | 180 |
| caagaaaaag | aaacgtgata | aaaattttta | ttgccttttt | cgacgaagaa | aagaaacga | 240 |
| ggcggtctct | tttttctttt | ccaaacccttt | agtacgggta | attaacgaca | ccctagagga | 300 |
| agaaagaggg | gaaatttagt | atgctgtgct | tgggtgtttt | gaagtggtac | ggcgatgcgc | 360 |
| ggagtccgag | aaaatctgga | agagtaaaaa | aggagtagaa | acattttgaa | gctatgagct | 420 |
| ccagctttg | ttccctttag | tgagggttaa | ttgcgcgctt | ggcgtaatca | tggtcatagc | 480 |
| tgtttcctgt | gtgaaattgt | tatccgctca | caattccaca | caacatagga | gccgaagca | 540 |
| taaagtgtaa | agcctggggt | gcctaatgag | tgaggtaact | cacattaatt | gcgttgcgct | 600 |
| cactgcccgc | tttccagtcg | ggaaacctgt | cgtgccagct | gcattaatga | atcggccaac | 660 |
| gcgcggggag | aggcggtttg | cgtattgggc | gctcttccga | gctcagttta | tcattatcaa | 720 |
| tactcgccat | ttcaaagaat | acgtaaataa | ttaatagtag | tgattttcct | aactttattt | 780 |
| agtcaaaaaa | ttagcctttt | aattctgctg | taacccgtac | atgcccaaaa | taggggcgg | 840 |
| gttacacaga | atatataaca | tcgtaggtgt | ctgggtgaac | agtttattcc | tggcatccac | 900 |
| taaatataat | ggagcccgct | ttttaagctg | gcatccagaa | aaaaaagaa | tcccagcacc | 960 |
| aaaatattgt | tttcttcacc | aaccatcagt | tcataggtcc | attctcttag | cgcaactaca | 1020 |
| gagaacaggg | gcacaaacag | gcaaaaaacg | ggcacaacct | caatggagtg | atgcaacctg | 1080 |
| cctggagtaa | atgatgacac | aaggcaattg | acccacgcat | gtatctatct | cattttctta | 1140 |
| caccttctat | taccttctgc | tctctctgat | ttggaaaaag | ctgaaaaaaa | aggttgaaac | 1200 |
| cagttccctg | aaattattcc | cctacttgac | taataagtat | ataaagacgg | taggtattga | 1260 |
| ttgtaattct | gtaaatctat | ttcttaaact | tcttaaattc | tacttttata | gttagtcttt | 1320 |
| tttttagttt | taaaacacca | gaacttagtt | tcgacggatt | ctagaggatc | cat | 1373 |

<210> SEQ ID NO 8
<211> LENGTH: 12851
<212> TYPE: DNA
<213> ORGANISM: artificial
<220> FEATURE:
<223> OTHER INFORMATION: vector

<400> SEQUENCE: 8

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accataccac | agcttttcaa | ttcaattcat | cattttttt | ttattctttt | ttttgatttc | 240 |
| ggtttctttg | aaatttttt | gattcggtaa | tctccgaaca | gaaggaagaa | cgaaggaagg | 300 |
| agcacagact | tagattggta | tatatacgca | tatgtagtgt | tgaagaaaca | tgaaattgcc | 360 |
| cagtattctt | aacccaactg | cacagaacaa | aaacctgcag | gaaacgaaga | taatcatgt | 420 |

```
cgaaagctac atataaggaa cgtgctgcta ctcatcctag tcctgttgct gccaagctat      480
ttaatatcat gcacgaaaag caaacaaact tgtgtgcttc attggatgtt cgtaccacca      540
aggaattact ggagttagtt gaagcattag gtcccaaaat ttgtttacta aaaacacatg      600
tggatatctt gactgatttt tccatggagg gcacagttaa gccgctaaag gcattatccg      660
ccaagtacaa ttttttactc ttcgaagaca gaaaatttgc tgacattggt aatacagtca      720
aattgcagta ctctgcgggt gtatacgaaa tagcagaatg ggcagacatt acgaatgcac      780
acggtgtggt gggcccaggt attgttagcg gtttgaagca ggcggcagaa gaagtaacaa      840
aggaacctag aggcctttg atgttagcag aattgtcatg caagggctcc ctatctactg       900
gagaatatac taagggtact gttgacattg cgaagagcga caaagatttt gttatcggct      960
ttattgctca aagagacatg ggtggaagag atgaaggtta cgattggttg attatgacac     1020
ccggtgtggg tttagatgac aagggagacg cattgggtca acagtataga accgtggatg     1080
atgtggtctc tacaggatct gacattatta ttgttggaag aggactattt gcaaagggaa     1140
gggatgctaa ggtagagggt gaacgttaca gaaaagcagg ctgggaagca tatttgagaa     1200
gatgcggcca gcaaaactaa aaaactgtat tataagtaaa tgcatgtata ctaaactcac     1260
aaattagagc ttcaatttaa ttatatcagt tattacccta tgcggtgtga aataccgcac     1320
agatgcgtaa ggagaaaata ccgcatcagg aaattgtaaa cgttaatatt ttgttaaaat     1380
tcgcgttaaa tttttgttaa atcagctcat tttttaacca ataggccgaa atcggcaaaa     1440
tcccttataa atcaaagaa tagaccgaga tagggttgag tgttgttcca gtttggaaca      1500
agagtccact attaaagaac gtggactcca acgtcaaagg gcgaaaaacc gtctatcagg     1560
gcgatggccc actacgtgaa ccatcaccct aatcaagttt tttggggtcg aggtgccgta     1620
aagcactaaa tcggaaccct aaagggagcc cccgatttag agcttgacgg ggaaagccgg     1680
cgaacgtggc gagaaaggaa gggaagaaag cgaaaggagc gggcgctagg gcgctggcaa     1740
gtgtagcggt cacgctgcgc gtaaccacca cacccgccgc gcttaatgcg ccgctacagg     1800
gcgcgtccat cgccattca ggctgcgcaa ctgttgggaa gggcgatcgg tgcgggcctc      1860
ttcgctatta cgccagctga attggagcga cctcatgcta tacctgagaa agcaacctga     1920
cctacaggaa agagttactc aagaataaga attttcgttt taaaacctaa gagtcacttt     1980
aaaatttgta tacacttatt tttttataa cttatttaat aataaaaatc ataaatcata      2040
agaaattcgc ttatttagaa gtgtcaacaa cgtatctacc aacgatttga ccctttttcca    2100 tcttttcgta aatttctggc aaggtagaca agccgacaac cttgattgga gacttgacca     2160
aacctctggc gaagaattgt taattaagag ctcagatctt atcgtcgtca tccttgtaat     2220
ccatcgatac tagtttagca aatcggaatc ggagctccgt tccattcctt gagacaatcc     2280
atcaacggat caataagttt accttcacac atagcagtga agaccttatc aaactcctct     2340 cccgagaca caaccttttc tccagtcaac aacttcgttc caagctcttc cctcacgaac      2400
ctatacaacg gatacgacct acattcctta atccggttag gaatcggcgc agttccattc     2460
ccataagccg ctctagccgc ttcaacttcc tttggaagca cagccttaag ctcctcttca     2520
aaagctccaa tcttttgaaa gatcgaagtc actgcattct tctcagtctc accgttggac     2580
aaagcgtgat caacaataac ttgtcttagt ctctgcatca acgggtacgt agcgctacaa     2640
ggatcatcca catacgtgaa cacttgctca cgatcaacaa ccttaagcaa gtccttctcg     2700
caaaaccttg acggatgtaa ctcaccgttg attccagtgg ttaacacttt cttagcaact     2760
tgagaaactg tgttcttcac agtttgtctc agattctcct ccaaatgtct caaatcaaca     2820
```

```
gcttgacata tccccacaag gaacgttgtt gacattagct taagaatatc cacagcttca    2880
gatgttttac gagacgagat caaaccaaga gagttcacat cttgattatg ttgctcagct    2940
gattgaacat ggcttgtgac tggattagcc aagtattgaa gctcagaaca ataagaagcc    3000
atagcaatct ctgctccttt gaatccataa tccaaacttg gattactcga agcagttaga    3060
ttcgaaggaa gtccattgtt gtagaaatca ttaacaagct cagagaattg agcaaacatt    3120
agcttcccaa tcgcagcaat cgccaatctc gtgttatcca tagaaactcc gattggtgtt    3180
ccttggaagt taccaccgtg aatcgccttg ttcctcgaaa catcgatcaa cggattatcg    3240
ttaacggagt tgatttcacg ctctatcgat ttcgtagctt gacggattac ttcaatttga    3300
ggacctagcc attgaggaga tgtacgaaga gcgtaacgat cttgttttgg tttctgcaat    3360
ggatccatct cgtgaacctt tgagctaatt tcatgtatg agcttccgtc gagtatgtgc     3420
tccattatcg ccgccgcttc gatttgtccg ggatgatgtt taaacgatg agtcagatga     3480
tcggtaaact caggttcccc gctcataacc tccgcgaaga tcgctgataa aacctccgct    3540
aacaccgctt ggacattcgc ttcgaataga accatcgacg ccattccaga tccaaccgcc    3600
gtgccattaa cgagagctaa accttcctta ggttgtaaat cgaagaatcc agtactgatt    3660
ccggctttct caaaagcttc tttcgcggtt agcgattcac cgtcgggacc ggtggctttg    3720
gaattaggac ggccggtgag aagtccggcg atgtaagaga gaggaacgag atcgccggag    3780
gcggtaatgg ttccacggag aggtagtgac ggagagatgt tgtggttgag gagacttgta    3840
atcgcttcga ggatctcgaa tcggatcccg gagtatcctt ggagaagagt gttgactctg    3900
acgagcatgg cggctcttgt ggcggattgc ggcagtgtgt gacatgtctc cttcgtgttt    3960
ccgaatattc cggcgttcaa aaatctaatg agttctgttt gtaatgcggt gccgttttg     4020
gttctccggt gagaagtagc accaaagccg gtggtgactc cgtaactgtc agtacctttg    4080
ttcatgctct ccataaccca atcactgcta gctttcacac cggctcttga agtctccgct    4140
aactcaacct taacgctgcc tcctacggtg gagatggcag caacttgtcc gatcgtcagt    4200
gtttctccgc caagattcac gactggtcta cgatactctt cgaccatctt cttcacttca    4260
tctaaatgac ttcctttcat ttgatccgct gctaaacccc aattcaatgg atctgccaaa    4320
gtcttcgtag taaccgccac ttttgtcttc tctcctccgc cgcacaacat tgcttcgatt    4380
tgatccatta cgtacgtcta gaaaacttag attagattgc tatgctttct ttctaatgag    4440
caagaagtaa aaaagttgt aatagaacaa gaaaaatgaa actgaaactt gagaaattga    4500
agaccgttta ttaacttaaa tatcaatggg aggtcatcga aagagaaaaa atcaaaaaa    4560
aaaattttca agaaaagaa acgtgataaa aatttttatt gccttttcg acgaagaaaa    4620
agaaacgagg cggtctcttt tttcttttcc aaacctttag tacgggtaat taacgacacc    4680
ctagaggaag aaagagggga aatttagtat gctgtgcttg ggtgttttga agtggtacgg    4740
cgatgcgcgg agtccgagaa atctggaag agtaaaaaag gagtagaaac attttgaagc     4800
tatgagctcc agcttttgtt ccctttagtg agggttaatt gcgcgcttgg cgtaatcatg    4860
gtcatagctg tttcctgtgt gaaattgtta tccgctcaca attccacaca acataggagc    4920
cggaagcata aagtgtaaag cctggggtgc ctaatgagtg aggtaactca cattaattgc    4980
gttgcgctca ctgcccgctt tccagtcggg aaacctgtcg tgccagctgc attaatgaat    5040
cggccaacgc gcggggagag gcggtttgcg tattgggcgc tcttccgagc tcagtttatc    5100
attatcaata ctcgccattt caagaatac gtaaataatt aatagtagtg attttcctaa     5160
ctttatttag tcaaaaatt agccttttaa ttctgctgta acccgtacat gcccaaaata    5220
```

```
gggggcgggt tacacagaat atataacatc gtaggtgtct gggtgaacag tttattcctg    5280
gcatccacta aatataatgg agcccgcttt ttaagctggc atccagaaaa aaaaagaatc    5340
ccagcaccaa aatattgttt tcttcaccaa ccatcagttc ataggtccat tctcttagcg    5400
caactacaga gaacagggc acaaacaggc aaaaacggg cacaacctca atggagtgat    5460
gcaacctgcc tggagtaaat gatgacacaa ggcaattgac ccacgcatgt atctatctca    5520
ttttcttaca ccttctatta ccttctgctc tctctgattt ggaaaaagct gaaaaaaag    5580 gttgaaacca gttccctgaa attattcccc tacttgacta ataagtatat aaagacggta    5640
ggtattgatt gtaattctgt aaatctattt cttaaacttc ttaaattcta cttttatagt    5700 tagtctttt tttagttta aaacaccaga acttagtttc gacggattct agagcggccg    5760
ctaaaatatg gacctcctct tgctggagaa gtctttaatc gccgtcttcg tggcggtgat    5820
tctcgccacg gtgatttcaa agctccgcgg caagaaattg aagctacctc caggtcctat    5880
accaattccg atcttcggaa actggcttca agtcggagat gatctcaacc accgtaatct    5940
cgtcgattac gctaagaaat tcggcgatct cttcctcctc cgtatgggtc agcgaaacct    6000
agtcgtcgtc tcctcaccgg atctaacaaa ggaagtgctc ctcactcaag gcgttgagtt    6060
tggatccaga acgagaaacg tcgtgttcga cattttcacc gggaaaggtc aagatatggt    6120
gttcactgtt tacggcgagc attggaggaa gatgagaaga atcatgacgg ttcctttctt    6180
caccaacaaa gttgttcaac agaatcgtga aggttgggag tttgaagcag ctagtgttgt    6240
tgaagatgtt aagaagaatc cagattctgc tacgaaagga atcgtgttga ggaaacgttt    6300
gcaattgatg atgtataaca atatgttccg tatcatgttc gatagaagat ttgagagtga    6360
ggatgatcct cttttcctta ggcttaaggc tttgaatggt gagagaagtc gattagctca    6420
gagctttgag tataactatg gagatttcat tcctatcctt agaccattcc tcagaggcta    6480
tttgaagatt tgtcaagatg tgaaagatcg aagaatcgct cttttcaaga agtactttgt    6540
tgatgagagg aagcaaattg cgagttctaa gcctacaggt agtgaaggat tgaaatgtgc    6600
cattgatcac atccttgaag ctgagcagaa gggagaaatc aacgaggaca atgttcttta    6660
catcgtcgag aacatcaatg tcgccgcgat tgagacaaca ttgtggtcta tcgagtgggg    6720
aattgcagag ctagtgaacc atcctgaaat ccagagtaag ctaaggaacg aactcgacac    6780
agttcttgga ccgggtgtgc aagtcaccga gcctgatctt cacaaacttc atacccttca    6840
agctgtggtt aaggagactc ttcgtctgag aatggcgatt cctctcctcg tgcctcacat    6900
gaacctccat gatgcgaagc tcgctggcta cgatatccca gcagaaagca aaatccttgt    6960
taatgcttgg tggctagcaa acaaccccaa cagctggaag aagcctgaag agtttagacc    7020
agagaggttc tttgaagaag aatcgcacgt ggaagctaac ggtaatgact tcaggtatgt    7080
gccatttggt gttggacgtc gaagctgtcc cgggattata ttggcattgc ctattttggg    7140
gatcaccatt ggtaggatgg tccagaactt cgagcttctt cctcctccag acagtctaa    7200 agtggatact agtgagaaag gtggacaatt cagcttgcac atccttaacc actccataat    7260
cgttatgaaa ccaaggaact gtccatctac tccatctact ccatctactc catctactag    7320
gagatccggt tctgggaatt caaaacgtgt cgagcctctt aagcctttgg ttattaagcc    7380
tcgtgaggaa gagattgatg atgggcgtaa gaaagttacc atcttttcg gtacacaaac    7440 tggtactgct gaaggttttg caaaggcttt aggagaagaa gctaaagcaa gatatgaaaa    7500
gaccagattc aaaatcgttg atttggatga ttacgcggct gatgatgatg agtatgagga    7560
gaaattgaag aaagaggatg tggctttctt cttcttagcc acatatggag atggtgagcc    7620
```

```
taccgacaat gcagcgagat tctacaaatg gttcaccgag gggaatgaca gaggagaatg   7680
gcttaagaac ttgaagtatg gagtgtttgg attaggaaac agacaatatg agcattttaa   7740
taaggttgcc aaagttgtag atgacattct tgtcgaacaa ggtgcacagc gtcttgtaca   7800
agttggtctt ggagatgatg accagtgtat tgaagatgac tttaccgctt ggcgagaagc   7860
attgtggccc gagcttgata caatactgag ggaagaaggg gatacagctg ttgccacacc   7920
atacactgca gctgtgttag aatacagagt ttctattcac gactctgaag atgccaaatt   7980
caatgatata aacatggcaa atgggaatgg ttacactgtg tttgatgctc aacatcctta   8040
caaagcaaat gtcgctgtta aagggagctc atactcccc gagtctgatc gttcttgtat    8100
ccatttggaa tttgacattg ctggaagtgg acttacgtat gaaactggag atcatgttgg   8160
tgtactttgt gataacttaa gtgaaactgt agatgaagct cttagattgc tggatatgtc   8220
acctgatact tatttctcac ttcacgctga aaagaagac ggcacaccaa tcagcagctc     8280
actgcctcct cccttccac cttgcaactt gagaacagcg cttacacgat atgcatgtct     8340
tttgagttct ccaaagaagt ctgctttagt tgcgttggct gctcatgcat ctgatcctac    8400
cgaagcagaa cgattaaaac accttgcttc acctgctgga aaggatgaat attcaaagtg    8460
ggtagtagag agtcaaagaa gtctacttga ggtgatggcc gagtttcctt cagccaagcc    8520
accacttggt gtcttcttcg ctggagttgc tccaaggttg cagcctaggt tctattcgat    8580
atcatcatcg cccaagattg ctgaaactag aattcacgtc acatgtgcac tggtttatga    8640
gaaaatgcca actggcagga ttcataaggg agtgtgttcc acttggatga agaatgctgt    8700
gccttacgag aagagtgaaa actgttcctc ggcgccgata tttgttaggc aatccaactt    8760
caagcttcct tctgattcta aggtaccgat catcatgatc ggtccaggga ctggattagc    8820
tccattcaga ggattccttc aggaaagact agcgttggta gaatctggtg ttgaacttgg    8880
gccatcagtt ttgttctttg gatgcagaaa ccgtagaatg gatttcatct acgaggaaga    8940
gctccagcga tttgttgaga gtggtgctct cgcagagcta agtgtcgcct tctctcgtga    9000
aggacccacc aaagaatacg tacagcacaca gatgatggac aaggcttctg atatctggaa    9060
tatgatctct caaggagctt atttatatgt ttgtggtgac gccaaaggca tggcaagaga    9120
tgttcacaga tctctccaca caatagctca agaacagggg tcaatggatt caactaaagc    9180
agagggcttc gtgaagaatc tgcaaacgag tggaagatat cttagagatg tatggtaagg    9240
taccgcggct agctaagatc cgctctaacc gaaaggaag gagttagaca acctgaagtc     9300
taggtcccta tttatttttt tatagttatg ttagtattaa gaacgttatt tatatttcaa    9360
atttttcttt tttttctgta cagacgcgtg tacgcatgta acattatact gaaaaccttg    9420
cttgagaagg ttttgggacg ctcgaagatc cagctgcatt aatgaatcgg ccaacgcgcg    9480
gggagaggcg gtttgcgtat tgggcgctct tccgcttcct cgctcactga ctcgctgcgc    9540
tcggtcgttc ggctgcggcg agcggtatca gctcactcaa aggcggtaat acggttatcc    9600
acagaatcag gggataacgc aggaaagaac atgtgagcaa aaggccagca aaaggccagg    9660
aaccgtaaaa aggccgcgtt gctggcgttt ttccataggc tccgcccccc tgacgagcat    9720
cacaaaaatc gacgctcaag tcagaggtgg cgaaacccga caggactata aagataccag    9780
gcgtttcccc ctggaagctc cctcgtgcgc tctcctgttc cgaccctgcc gcttaccgga    9840
tacctgtccg cctttctccc ttcgggaagc gtggcgcttt ctcatagctc acgctgtagg    9900
tatctcagtt cggtgtaggt cgttcgctcc aagctgggct gtgtgcacga accccccgtt    9960
cagcccgacc gctgcgcctt atccggtaac tatcgtcttg agtccaaccc ggtaagacac   10020
```

```
gacttatcgc cactggcagc agccactggt aacaggatta gcagagcgag gtatgtaggc   10080
ggtgctacag agttcttgaa gtggtggcct aactacggct acactagaag gacagtattt   10140
ggtatctgcg ctctgctgaa gccagttacc ttcggaaaaa gagttggtag ctcttgatcc   10200
ggcaaacaaa ccaccgctgg tagcggtggt ttttttgttt gcaagcagca gattacgcgc   10260
agaaaaaaag gatctcaaga agatcctttg atcttttcta cggggtctga cgctcagtgg   10320
aacgaaaact cacgttaagg gattttggtc atgagattat caaaaaggat cttcacctag   10380
atccttttaa attaaaaatg aagttttaaa tcaatctaaa gtatatatga gtaaacttgg   10440
tctgacagtt accaatgctt aatcagtgag gcacctatct cagcgatctg tctatttcgt   10500
tcatccatag ttgcctgact ccccgtcgtg tagataacta cgatacggga gggcttacca   10560
tctggcccca gtgctgcaat gataccgcga gacccacgct caccggctcc agatttatca   10620
gcaataaacc agccagccgg aagggccgag cgcagaagtg gtcctgcaac tttatccgcc   10680
tccatccagt ctattaattg ttgccgggaa gctagagtaa gtagttcgcc agttaatagt   10740
ttgcgcaacg ttgttgccat tgctacaggc atcgtggtgt cacgctcgtc gtttggtatg   10800
gcttcattca gctccggttc ccaacgatca aggcgagtta catgatcccc catgttgtgc   10860
aaaaaagcgg ttagctcctt cggtcctccg atcgttgtca gaagtaagtt ggccgcagtg   10920
ttatcactca tggttatggc agcactgcat aattctctta ctgtcatgcc atccgtaaga   10980
tgcttttctg tgactggtga gtactcaacc aagtcattct gagaatagtg tatgcggcga   11040
ccgagttgct cttgcccggc gtcaatacgg gataataccg cgccacatag cagaacttta   11100
aaagtgctca tcattggaaa acgttcttcg gggcgaaaac tctcaaggat cttaccgctg   11160
ttgagatcca gttcgatgta acccactcgt gcacccaact gatcttcagc atcttttact   11220
ttcaccagcg tttctgggtg agcaaaaaca ggaaggcaaa atgccgcaaa aaagggaata   11280
agggcgacac ggaaatgttg aatactcata ctcttccttt ttcaatatta ttgaagcatt   11340
tatcagggtt attgtctcat gagcggatac atatttgaat gtatttagaa aaataaacaa   11400
ataggggttc cgcgcacatt tccccgaaaa gtgccacctg aacgaagcat ctgtgcttca   11460
ttttgtagaa caaaaatgca acgcgagagc gctaatttt caaacaaaga atctgagctg   11520 cattttaca gaacagaaat gcaacgcgaa agcgctattt taccaacgaa gaatctgtgc   11580 ttcattttg taaacaaaa atgcaacgcg agagcgctaa ttttcaaac aaagaatctg   11640 agctgcattt ttacagaaca gaaatgcaac gcgagagcgc tattttacca caaagaatc   11700 tatacttctt ttttgttcta caaaaatgca tcccgagagc gctattttc taacaaagca   11760 tcttagatta cttttttttct cctttgtgcg ctctataatg cagtctcttg ataacttttt   11820
gcactgtagg tccgttaagg ttagaagaag gctactttgg tgtctatttt ctcttccata   11880
aaaaaagcct gactccactt cccgcgttta ctgattacta gcgaagctgc gggtgcattt   11940
tttcaagata aaggcatccc cgattatatt ctataccgat gtggattgcg catactttgt   12000
gaacagaaag tgatagcgtt gatgattctt cattggtcag aaaattatga acggtttctt   12060
ctattttgtc tctatatact acgtatagga aatgtttaca ttttcgtatt gttttcgatt   12120
cactctatga atagttctta ctacaatttt tttgtctaaa gagtaatact agagataaac   12180
ataaaaaatg tagaggtcga gtttagatgc aagttcaagg agcgaaaggt ggatgggtag   12240
gttatatagg gatatagcac agagatatat agcaaagaga tacttttgag caatgtttgt   12300
ggaagcggta ttcgcaatat tttagtagct cgttacagtc cggtgcgttt ttggttttt   12360 gaaagtgcgt cttcagagcg cttttggttt tcaaaagcgc tctgaagttc ctatactttc   12420
```

```
tagagaatag gaacttcgga ataggaactt caaagcgttt ccgaaaacga gcgcttccga    12480
aaatgcaacg cgagctgcgc acatacagct cactgttcac gtcgcaccta tatctgcgtg    12540
ttgcctgtat atatatatac atgagaagaa cggcatagtg cgtgtttatg cttaaatgcg    12600 tactatatg cgtctattta tgtaggatga aaggtagtct agtacctcct gtgatattat     12660
cccattccat gcggggtatc gtatgcttcc ttcagcacta cccttttagct gttctatatg   12720 ctgccactcc tcaattggat tagtctcatc cttcaatgct atcatttcct ttgatattgg    12780
atcatactaa gaaaccatta ttatcatgac attaacctat aaaaataggc gtatcacgag    12840
gccctttcgt c                                                         12851

<210> SEQ ID NO 9
<211> LENGTH: 10157
<212> TYPE: DNA
<213> ORGANISM: artificial
<220> FEATURE:
<223> OTHER INFORMATION: vector

<400> SEQUENCE: 9
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tcttttttcta   300 ttactcttgg cctcctctag tacactctat attttttttat gcctcggtaa tgattttcat   360 ttttttttt cccctagcgg atgactcttt tttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tccctagcg atagagcact      600 cgatcttccc agaaaagag gcagaagcag tagcagaaca ggccacacaa tcgcaagtga     660
ttaacgtcca cacaggtata gggtttctgg accatatgat acatgctctg ccaagcatt     720 ccggctggtc gctaatcgtt gagtgcattg gtgacttaca catagacgac catcacacca    780
ctgaagactg cgggattgct ctcggtcaag ctttttaaaga ggccctactg gcgcgtggag   840
taaaaaggtt tggatcagga tttgcgcctt tggatgaggc actttccaga gcggtggtag     900
atctttcgaa caggccgtac gcagttgtcg aacttggttt gcaaagggag aaagtaggag     960
atctctcttg cgagatgatc ccgcattttc ttgaaagctt tgcagaggct agcagaatta    1020
ccctccacgt tgattgtctg cgaggcaaga atgatcatca ccgtagtgag agtgcgttca    1080
aggctcttgc ggttgccata agagaagcca cctcgcccaa tggtaccaac gatgttccct    1140
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320 cctttttttct ttttgctttt tcttttttttt tctcttgaac tcgacggatc tatgcggtgt    1380
gaaataccgc acagatgcgt aaggagaaaa taccgcatca ggaaattgta aacgttaata    1440
ttttgttaaa attcgcgtta aattttttgtt aaatcagctc attttttaac caataggccg    1500
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
```

```
ccgtctatca gggcgatggc ccactacgtg aaccatcacc ctaatcaagt ttttggggt    1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctgaattg gagcgacctc atgctatacc   1980
tgagaaagca acctgaccta caggaaagag ttactcaaga ataagaattt tcgttttaaa   2040
acctaagagt cactttaaaa tttgtataca cttatttttt ttataactta tttaataata   2100
aaaatcataa atcataagaa attcgcttat ttagaagtgt caacaacgta tctaccaacg   2160
atttgaccct tttccatctt ttcgtaaatt tctggcaagg tagacaagcc gacaaccttg   2220
attggagact tgaccaaacc tctggcgaag aattgttaat taagagctca gatcttatcg   2280
tcgtcatcct tgtaatccat cgatactagt ctagttcatt aatccatttg ctagtcttgc   2340
tcttagatcc ttcctcaata tcttccctga tggagcttta ggaatagagt cagtgaagaa   2400
cactttgttg attctcttat aaaacacaac ctgttttgac acgaattgct tgatttcatc   2460
ttcggatata tttgaatctt tcgatctcac cacaaacgca acaggaacct caccagcatc   2520
ttcttccttc atggcgacga cagcaacatc attgatttct ggatgaccta tgaggagaga   2580
ctctagctca gctggagcca cttgaaatcc tttgtacttg atgagttctt tcaatctatc   2640
cacaatgaaa agctcgtcgt catcatcgat aaatccgacg tctccagtgt gaagccaacc   2700
atctttatcg atcgtcgatg ccgtggccaa ggggtcattg agatagcctt tcatgatttg   2760
gttgccacgg atgcatattt cgccgggttt gttcctaggc aaagaatctc ctgtgtctgg   2820
atcaagtatc ttcatctcgg cgttcctcac caccgtacca catgctcctg acttcactgg   2880
aaacggctct ttagcaaacc ctaacgacat tgctagcacc ggacctgctt ctgtcatccc   2940
atagccctga ccaagcttgg cgttaggaaa cttagcacta atagcatctt caagctcctt   3000
accaagagga gctgctccag acttaaccat cctaaccgag ctcagatcat acttctccgt   3060
ctccggcgac ttcgcgatag ctaaaacgat cggtggcacg accatagcca ccgtgacttt   3120
acacctttgt atctgctcta acaagagagt gatttcgaac ttaggcatta tcaagatcgt   3180
ggcaccaact ctgagactac agagcatgat ggagttgaga gcgtatatat ggaacatagg   3240
caagacacag aggatcacgt cgtctctgtt gaagtaaaga ttcggattct cgccgtcgac   3300
ttgctgcgcc acgctcgtga ctagaccttt gtgtgttagc atcactcctt tggggagacc   3360
cgtcgtgccg gatgagaaag gaagcgccac gacgtcttct ggcgaaatct tctccggtat   3420
tgagtccact cgtggttctt cggactgagt taactcggag aaacggaggc agttttcggg   3480
gatggcgtcg gagtcggtgg tgacgatcaa aacgccgtcg ttttggaggt tcttgatttt   3540
atcgacgtaa cggattgag tgacgatgag tttcgccgcg gaggctttgg cttgtttaga   3600
aatctccgcc ggagtgaaga acgggttcgc ggaggtggtg attgcgccga tgaaggaggc   3660
ggcaaggaaa gtgaggacta cttcaggaga gttcggagg aggatcatta caacgtcgtg   3720
ttgcttcacg ccgaggttat gaagaccggc ggcgagtttc cgagatgtta cgtggacatc   3780
ggcgtaggt tatacttcgc cggtgggacc gttgatcaag catggcttag cggcgaactc   3840
tgagatattt tcgaagatgt agtcgtggag tgggaggtgg ttagggatgt atatatcagg   3900
caatctcgat cggaaaatga cgtcattact acactgtttc tgatcattct gatcattgac   3960
tatcacatct tgtgtcgtca tgaattctct agaaaactta gattagattg ctatgctttc   4020
```

```
tttctaatga gcaagaagta aaaaaagttg taatagaaca agaaaaatga aactgaaact    4080
tgagaaattg aagaccgttt attaacttaa atatcaatgg gaggtcatcg aaagagaaaa    4140
aaatcaaaaa aaaaattttc aagaaaaaga aacgtgataa aaatttttat tgcctttttc    4200
gacgaagaaa aagaaacgag gcggtctctt ttttcttttc caaacccttta gtacgggtaa    4260 ttaacgacac cctagaggaa gaaagagggg aaatttagta tgctgtgctt gggtgttttg    4320
aagtggtacg gcgatgcgcg gagtccgaga aaatctggaa gagtaaaaaa ggagtagaaa    4380
cattttgaag ctatgagctc cagcttttgt tcccttagt gagggttaat tgcgcgcttg    4440
gcgtaatcat ggtcatagct gtttcctgtg tgaaattgtt atccgctcac aattccacac    4500
aacataggag ccggaagcat aaagtgtaaa gcctggggtg cctaatgagt gaggtaactc    4560
acattaattg cgttgcgctc actgcccgct ttccagtcgg gaaacctgtc gtgccagctg    4620
cattaatgaa tcggccaacg cgcggggaga ggcggtttgc gtattgggcg ctcttccgag    4680
ctcagtttat cattatcaat actcgccatt tcaaagaata cgtaaataat taatagtagt    4740
gattttccta actttatta gtcaaaaaat tagccttta attctgctgt aacccgtaca    4800
tgcccaaaat aggggcggg ttacacagaa tatataacat cgtaggtgtc tgggtgaaca    4860
gtttattcct ggcatccact aaatataatg gagcccgctt tttaagctgg catccagaaa    4920 aaaaagaat cccagcacca aaatattgtt ttcttcacca accatcagtt cataggtcca    4980
ttctcttagc gcaactacag agaacagggg cacaaacagg caaaaaacgg gcacaacctc    5040
aatggagtga tgcaacctgc ctggagtaaa tgatgacaca aggcaattga cccacgcatg    5100
tatctatctc atttcttac accttctatt accttctgct ctctctgatt tggaaaagc    5160 tgaaaaaaaa ggttgaaacc agttccctga aattattccc ctacttgact aataagtata    5220
taaagacggt aggtattgat tgtaattctg taaatctatt tcttaaactt cttaaattct    5280
acttttatag ttagtctttt ttttagtttt aaaacaccag aacttagttt cgacggattc    5340
tagaggatcc atggcatccg tagaggagtt cagaaatgca cagagggcaa aaggtccagc    5400
aaccatattg gctattggaa cagccacccc tgatcactgt gtttatcaat ctgattacgc    5460
tgattactat ttcagagtaa ctaaaagtga acatatgaca gaacttaaga aaagtttaa    5520 tagaatttgt gataaatcta tgataaagaa aagatacata catctaactg aagaaatgtt    5580
agaggaacat ccaaatatag gtgcatatat ggcaccatct ttgaatatta gacaagaaat    5640
cataacagcc gaggtaccta gactaggtag agacgcagcc ttgaaagctt taaggaatg    5700 gggacaacca aaatctaaga ttacacattt ggttttctgt acaacttccg gtgtcgaaat    5760
gccaggtgct gattataaac tagcaaacct attgggatta gagacctctg ttagaagagt    5820
tatgttgtat catcaaggtt gttacgccgg aggtacagtg cttagaactg ctaaggattt    5880
ggcagaaaat aacgccggtg ctagggtttt agtcgtctgc agtgaaatca ctgtcgtaac    5940
tttcagaggt ccatcagaag atgctctaga cagtttggtc ggacaagcat tgtttggcga    6000
tggatcttcc gccgtaattg taggcagcga tcctgatgtg tccattgaaa gaccactatt    6060
tcaattagtt tctgctgctc aaactttat tccaaattcc gccggtgcca tagcaggaaa    6120
cttgagagaa gttggtttga cttttcattt gtggcctaat gtcccaacct taatttcaga    6180
aaacatcgaa aaatgcttaa ctcaagcctt tgacccattg gcataagcg actgaactc    6240 attgttttgg attgctcatc caggtggtcc agcaatttta gacgcagtgg aggcaaaact    6300
aaacttagag aagaaaaagt tggaagctac aagcacgtt ctatcagagt atggcaacat    6360
gagctctgcc tgcgttttat tcattctaga tgagatgagg aagaagtctt taagggtga    6420
```

```
aaaagccaca accggagaag gtttagattg gggtgttcta tttggtttcg gtcctggctt    6480
aacaattgag acagtggtgt tacactctgt tccaactgtc actaactaat gactcgagta    6540
agcttggtac cgcggctagc taagatccgc tctaaccgaa aaggaaggag ttagacaacc    6600
tgaagtctag gtccctattt attttttttat agttatgtta gtattaagaa cgttatttat    6660
atttcaaatt tttctttttt ttctgtacag acgcgtgtac gcatgtaaca ttatactgaa    6720
aaccttgctt gagaaggttt tgggacgctc gaagatccag ctgcattaat gaatcggcca    6780
acgcgcgggg agaggcggtt tgcgtattgg gcgctcttcc gcttcctcgc tcactgactc    6840
gctgcgctcg gtcgttcggc tgcggcgagc ggtatcagct cactcaaagg cggtaatacg    6900
gttatccaca gaatcagggg ataacgcagg aaagaacatg tgagcaaaag gccagcaaaa    6960
ggccaggaac cgtaaaaagg ccgcgttgct ggcgtttttc cataggctcc gcccccctga    7020
cgagcatcac aaaaatcgac gctcaagtca gaggtggcga aacccgacag gactataaag    7080
ataccaggcg tttccccctg gaagctccct cgtgcgctct cctgttccga ccctgccgct    7140
taccggatac ctgtccgcct ttctcccttc gggaagcgtg gcgctttctc atagctcacg    7200
ctgtaggtat ctcagttcgg tgtaggtcgt tcgctccaag ctgggctgtg tgcacgaacc    7260
ccccgttcag cccgaccgct gcgccttatc cggtaactat cgtcttgagt ccaacccggt    7320
aagacacgac ttatcgccac tggcagcagc cactggtaac aggattagca gagcgaggta    7380
tgtaggcggt gctacagagt tcttgaagtg gtggcctaac tacggctaca ctagaaggac    7440
agtatttggt atctgcgctc tgctgaagcc agttaccttc ggaaaaagag ttggtagctc    7500
ttgatccggc aaacaaacca ccgctggtag cggtggtttt tttgtttgca agcagcagat    7560
tacgcgcaga aaaaaaggat ctcaagaaga tcctttgatc ttttctacgg ggtctgacgc    7620
tcagtggaac gaaaactcac gttaagggat tttggtcatg agattatcaa aaaggatctt    7680
cacctagatc cttttaaatt aaaaatgaag ttttaaatca atctaaagta tatatgagta    7740
aacttggtct gacagttacc aatgcttaat cagtgaggca cctatctcag cgatctgtct    7800
atttcgttca tccatagttg cctgactccc cgtcgtgtag ataactacga tacgggaggg    7860
cttaccatct ggccccagtg ctgcaatgat accgcgagac ccacgctcac cggctccaga    7920
tttatcagca ataaaccagc cagccggaag ggccgagcgc agaagtggtc ctgcaacttt    7980
atccgcctcc atccagtcta ttaattgttg ccgggaagct agagtaagta gttcgccagt    8040
taatagtttg cgcaacgttg ttgccattgc tacaggcatc gtggtgtcac gctcgtcgtt    8100
tggtatggct tcattcagct ccggttccca acgatcaagg cgagttacat gatccccat    8160 gttgtgcaaa aaagcggtta gctccttcgg tcctccgatc gttgtcagaa gtaagttggc    8220
cgcagtgtta tcactcatgg ttatggcagc actgcataat tctcttactg tcatgccatc    8280
cgtaagatgc ttttctgtga ctggtgagta ctcaaccaag tcattctgag aatagtgtat    8340
gcggcgaccg agttgctctt gcccggcgtc aatacgggat aataccgcgc cacatagcag    8400
aactttaaaa gtgctcatca ttggaaaacg ttcttcgggg cgaaaactct caaggatctt    8460
accgctgttg agatccagtt cgatgtaacc cactcgtgca cccaactgat cttcagcatc    8520
ttttactttc accagcgttt ctgggtgagc aaaaacagga aggcaaaatg ccgcaaaaaa    8580
gggaataagg gcgacacgga aatgttgaat actcatactc ttcctttttc aatattattg    8640
aagcatttat cagggttatt gtctcatgag cggatacata tttgaatgta tttagaaaaa    8700
taaacaaata ggggttccgc gcacatttcc ccgaaaagtg ccacctgaac gaagcatctg    8760
tgcttcattt tgtagaacaa aaatgcaacg cgagagcgct aatttttcaa acaaagaatc    8820
```

-continued

```
tgagctgcat ttttacagaa cagaaatgca acgcgaaagc gctatttac caacgaagaa      8880 tctgtgcttc attttgtaa aacaaaaatg caacgcgaga gcgctaattt ttcaaacaaa      8940
gaatctgagc tgcatttta cagaacagaa atgcaacgcg agagcgctat tttaccaaca      9000
aagaatctat acttctttt tgttctacaa aaatgcatcc cgagagcgct attttctaa       9060 caaagcatct tagattactt ttttctcct ttgtgcgctc tataatgcag tctcttgata      9120 acttttgca ctgtaggtcc gttaaggtta gaagaaggct actttggtgt ctatttctc       9180 ttccataaaa aaagcctgac tccacttccc gcgtttactg attactagcg aagctgcggg    9240
tgcatttttt caagataaag gcatccccga ttatattcta taccgatgtg gattgcgcat   9300
actttgtgaa cagaaagtga tagcgttgat gattcttcat tggtcagaaa attatgaacg   9360
gtttcttcta ttttgtctct atatactacg tataggaaat gtttacattt tcgtattgtt    9420
ttcgattcac tctatgaata gttcttacta caatttttt gtctaaagag taatactaga    9480
gataaacata aaaaatgtag aggtcgagtt tagatgcaag ttcaaggagc gaaaggtgga    9540
tgggtaggtt atatagggat atagcacaga gatatatagc aaagagatac ttttgagcaa    9600
tgtttgtgga agcggtattc gcaatatttt agtagctcgt tacagtccgg tgcgttttg     9660 gtttttgaa agtgcgtctt cagagcgctt ttggttttca aaagcgctct gaagttccta    9720
tactttctag agaataggaa cttcggaata ggaacttcaa agcgtttccg aaaacgagcg    9780
cttccgaaaa tgcaacgcga gctgcgcaca tacagctcac tgttcacgtc gcacctatat    9840
ctgcgtgttg cctgtatata tatatacatg agaagaacgg catagtgcgt gtttatgctt    9900
aaatgcgtac ttatatgcgt ctatttatgt aggatgaaag gtagtctagt acctcctgtg    9960
atattatccc attccatgcg gggtatcgta tgcttccttc agcactaccc tttagctgtt   10020
ctatatgctg ccactcctca attggattag tctcatcctt caatgctatc atttccttg    10080 atattggatc atctaagaaa ccattattat catgacatta acctataaaa ataggcgtat   10140
cacgaggccc tttcgtc                                                   10157
```

<210> SEQ ID NO 10
<211> LENGTH: 39
<212> TYPE: DNA
<213> ORGANISM: artificial
<220> FEATURE:
<223> OTHER INFORMATION: primer

<400> SEQUENCE: 10

```
cggaattccg tacgtaatgg atcaaatcga agcaatgtt                            39
```

<210> SEQ ID NO 11
<211> LENGTH: 29
<212> TYPE: DNA
<213> ORGANISM: artificial
<220> FEATURE:
<223> OTHER INFORMATION: primer

<400> SEQUENCE: 11

```
cgactagttt agcaaatcgg aatcggagc                                       29
```

<210> SEQ ID NO 12
<211> LENGTH: 43
<212> TYPE: DNA
<213> ORGANISM: artificial
<220> FEATURE:
<223> OTHER INFORMATION: primer

<400> SEQUENCE: 12

```
cgctcgaggc ggccgctaaa atatggacct cctcttgctg gag            43
```

<210> SEQ ID NO 13
<211> LENGTH: 58
<212> TYPE: DNA
<213> ORGANISM: artificial
<220> FEATURE:
<223> OTHER INFORMATION: primer

<400> SEQUENCE: 13

```
agtagatgga gtagatggag tagatggagt agatggacag ttccttggtt tcataacg   58
```

<210> SEQ ID NO 14
<211> LENGTH: 55
<212> TYPE: DNA
<213> ORGANISM: artificial
<220> FEATURE:
<223> OTHER INFORMATION: primer

<400> SEQUENCE: 14

```
ccatctactc catctactcc atctactcca tctactagga gatccggttc tggga       55
```

<210> SEQ ID NO 15
<211> LENGTH: 37
<212> TYPE: DNA
<213> ORGANISM: artificial
<220> FEATURE:
<223> OTHER INFORMATION: primer

<400> SEQUENCE: 15

```
cgggtaccat ttaccataca tctctaagat atcttcc                   37
```

<210> SEQ ID NO 16
<211> LENGTH: 40
<212> TYPE: DNA
<213> ORGANISM: artificial
<220> FEATURE:
<223> OTHER INFORMATION: primer

<400> SEQUENCE: 16

```
gcgaattctt atgacgacac aagatgtgat agtcaatgat                40
```

<210> SEQ ID NO 17
<211> LENGTH: 41
<212> TYPE: DNA
<213> ORGANISM: artificial
<220> FEATURE:
<223> OTHER INFORMATION: primer

<400> SEQUENCE: 17

```
gcactagtat cctagttcat taatccattt gctagtcttg c              41
```

<210> SEQ ID NO 18
<211> LENGTH: 41
<212> TYPE: DNA
<213> ORGANISM: artificial
<220> FEATURE:
<223> OTHER INFORMATION: primer

<400> SEQUENCE: 18

```
gcgagctcag tttatcatta tcaatactcg ccatttcaaa g              41
```

<210> SEQ ID NO 19
<211> LENGTH: 46
<212> TYPE: DNA
<213> ORGANISM: artificial
<220> FEATURE:

<223> OTHER INFORMATION: primer

<400> SEQUENCE: 19
cgtctagaat ccgtcgaaac taagttctgg tgttttaaaa ctaaaa                    46

<210> SEQ ID NO 20
<211> LENGTH: 44
<212> TYPE: DNA
<213> ORGANISM: artificial
<220> FEATURE:
<223> OTHER INFORMATION: primer

<400> SEQUENCE: 20
gcgagctcat agcttcaaaa tgtttctact cctttttac tctt                       44

<210> SEQ ID NO 21
<211> LENGTH: 45
<212> TYPE: DNA
<213> ORGANISM: artificial
<220> FEATURE:
<223> OTHER INFORMATION: primer

<400> SEQUENCE: 21
cgtctagaaa acttagatta gattgctatg ctttctttct aatga                     45

<210> SEQ ID NO 22
<211> LENGTH: 50
<212> TYPE: DNA
<213> ORGANISM: artificial
<220> FEATURE:
<223> OTHER INFORMATION: primer

<400> SEQUENCE: 22
ttgcgtattg ggcgctcttc cgagctcagt ttatcattat caatactcgc                50

<210> SEQ ID NO 23
<211> LENGTH: 35
<212> TYPE: DNA
<213> ORGANISM: artificial
<220> FEATURE:
<223> OTHER INFORMATION: primer

<400> SEQUENCE: 23
atggatcctc tagaatccgt cgaaactaag ttctg                                35

<210> SEQ ID NO 24
<211> LENGTH: 41
<212> TYPE: DNA
<213> ORGANISM: artificial
<220> FEATURE:
<223> OTHER INFORMATION: primer

<400> SEQUENCE: 24
atgaattctc tagaaaactt agattagatt gctatgcttt c                         41

<210> SEQ ID NO 25
<211> LENGTH: 44
<212> TYPE: DNA
<213> ORGANISM: artificial
<220> FEATURE:
<223> OTHER INFORMATION: primer

<400> SEQUENCE: 25
tgataatgat aaactgagct cggaagagcg cccaatacgc aaac                      44

<210> SEQ ID NO 26

```
<211> LENGTH: 35
<212> TYPE: DNA
<213> ORGANISM: artificial
<220> FEATURE:
<223> OTHER INFORMATION: primer

<400> SEQUENCE: 26
atggatcctc tagaatccgt cgaaactaag ttctg                               35

<210> SEQ ID NO 27
<211> LENGTH: 41
<212> TYPE: DNA
<213> ORGANISM: artificial
<220> FEATURE:
<223> OTHER INFORMATION: primer

<400> SEQUENCE: 27
gccgtacgtc tagaaaactt agattagatt gctatgcttt c                        41

<210> SEQ ID NO 28
<211> LENGTH: 38
<212> TYPE: DNA
<213> ORGANISM: artificial
<220> FEATURE:
<223> OTHER INFORMATION: primer

<400> SEQUENCE: 28
attgcggccg ctctagaatc cgtcgaaact aagttctg                            38

<210> SEQ ID NO 29
<211> LENGTH: 39
<212> TYPE: DNA
<213> ORGANISM: artificial
<220> FEATURE:
<223> OTHER INFORMATION: primer

<400> SEQUENCE: 29
cggaattccg tacgtaatgg atcaaatcga agcaatgtt                           39

<210> SEQ ID NO 30
<211> LENGTH: 29
<212> TYPE: DNA
<213> ORGANISM: artificial
<220> FEATURE:
<223> OTHER INFORMATION: primer

<400> SEQUENCE: 30
cgactagttt agcaaatcgg aatcggagc                                      29

<210> SEQ ID NO 31
<211> LENGTH: 43
<212> TYPE: DNA
<213> ORGANISM: artificial
<220> FEATURE:
<223> OTHER INFORMATION: primer

<400> SEQUENCE: 31
cgctcgaggc ggccgctaaa atatggacct cctcttgctg gag                      43

<210> SEQ ID NO 32
<211> LENGTH: 58
<212> TYPE: DNA
<213> ORGANISM: artificial
<220> FEATURE:
<223> OTHER INFORMATION: primer

<400> SEQUENCE: 32
```
agtagatgga gtagatggag tagatggagt agatggacag ttccttggtt tcataacg    58

<210> SEQ ID NO 33
<211> LENGTH: 55
<212> TYPE: DNA
<213> ORGANISM: artificial
<220> FEATURE:
<223> OTHER INFORMATION: primer

<400> SEQUENCE: 33
ccatctactc catctactcc atctactcca tctactagga gatccggttc tggga    55

<210> SEQ ID NO 34
<211> LENGTH: 37
<212> TYPE: DNA
<213> ORGANISM: artificial
<220> FEATURE:
<223> OTHER INFORMATION: primer

<400> SEQUENCE: 34
cgggtaccat ttaccataca tctctaagat atcttcc    37

<210> SEQ ID NO 35
<211> LENGTH: 43
<212> TYPE: DNA
<213> ORGANISM: artificial
<220> FEATURE:
<223> OTHER INFORMATION: primer

<400> SEQUENCE: 35
cgctcgaggc ggccgctaaa atatggacct cctcttgctg gag    43

<210> SEQ ID NO 36
<211> LENGTH: 37
<212> TYPE: DNA
<213> ORGANISM: artificial
<220> FEATURE:
<223> OTHER INFORMATION: primer

<400> SEQUENCE: 36
cgggtaccat ttaccataca tctctaagat atcttcc    37

<210> SEQ ID NO 37
<211> LENGTH: 41
<212> TYPE: DNA
<213> ORGANISM: artificial
<220> FEATURE:
<223> OTHER INFORMATION: primer

<400> SEQUENCE: 37
atgaattctc tagaaaactt agattagatt gctatgcttt c    41

<210> SEQ ID NO 38
<211> LENGTH: 1536
<212> TYPE: DNA
<213> ORGANISM: artificial
<220> FEATURE:
<223> OTHER INFORMATION: codon optimised gene

<400> SEQUENCE: 38
atgacacagg tagttgaaag gcaggcagat aggcttagtt ccagggaata tcttgccagg    60
gtcgtcaggt ccgctggttg ggatgctggt ttgacttcct gtactgatga ggaaatcgtg   120
agaatgggtg ctagtgccag aacaattgaa gagtacttga agtccgataa acctatatac   180
ggcttaacac aaggatttgg tccacttgtt ctatttgatg ccgatagtga attagagcaa   240

```
ggaggttctt taatctctca tctaggtaca ggccaaggtg ctcctttggc cccagaagtg      300
tcaagactaa tcttatggtt gagaatacag aatatgagaa aaggttattc cgcagtgtca      360
cctgtattct ggcagaagtt agccgatcta tggaataagg gtttcacacc agctattcca      420
aggcacggta ctgtctccgc atctggcgat ttgcagccac ttgctcatgc tgctttagca      480
ttcactggcg ttggagaagc atggacaaga gatgctgacg gcagatggag cactgttcct      540
gcagtagacg ctttggctgc ttttgggtgca gaaccatttg attggccagt tagagaggca     600
ttagcttttg ttaatggtac tggcgcctca ttggcagtag ccgtgctaaa ccataggagt      660
gctttaagat tagtgagagc ctgtgccgtg ttgtccgcaa ggttagccac attgcttggt      720
gccaatcctg agcattatga tgtaggtcat ggcgttgcaa gaggccaagt tggtcaattg      780
actgcagcag aatggatcag gcaaggttta cctagaggta tggtcagaga cggaagtagg      840
ccattgcaag aaccatactc cttaagatgt gctcctcaag ttttaggtgc cgttttggac      900
cagttagatg gagctggtga cgtattagct agggaagtcg acggttgtca ggacaatcct      960
ataacttacg aaggagagtt gttgcatggt ggtaatttcc atgcaatgcc agttggtttc     1020
gcatctgatc aaataggttt agcaatgcat atggccgctt acttggcaga aaggcagctt     1080
ggtttattag ttagccctgt tacaaacggt gaccttccac caatgttaac ccctagggct     1140
ggtagaggcg caggactagc aggtgtgcag atatccgcta ccagttttgt tagtagaatt     1200
aggcagttgg tgtttcctgc aagcttgaca actttgccta ccaacggatg gaatcaagat     1260
cacgtcccaa tggcattgaa tggcgcaaat tcagtattcg aagccttaga gttgggatgg     1320
ttaactgttg gtagcttggc agtaggtgtt gcccaattag ccgccatgac aggtcacgct     1380
gctgagggtg tttgggcaga acttgctggt atttgccctc cacttgatgc tgatagacct     1440
ttgggagcag aagtgagggc tgctagggat ctttttgtctg cccacgctga tcaattgtta     1500
gtcgatgaag ctgatggaaa agacttcgga taatga                               1536
```

<210> SEQ ID NO 39
<211> LENGTH: 1671
<212> TYPE: DNA
<213> ORGANISM: Arabidopsis thaliana

<400> SEQUENCE: 39

```
atgacgacac aagatgtgat agtcaatgat cagaatgatc agaaacagtg tagtaatgac      60 gtcatttttcc gatcgagatt gcctgatata tacatcccta accacctccc actccacgac     120
tacatcttcg aaaatatctc agagttcgcc gctaagccat gcttgatcaa cggtcccacc     180
ggcgaagtat acacctacgc cgatgtccac gtaacatctc ggaaactcgc cgccggtctt     240 cataaccctcg cgctgaagca acacgacgtt gtaatgatcc tcctcccgaa ctctcctgaa     300
gtagtcctca ctttccttgc cgcctccttc atcggcgcaa tcaccacctc cgcgaacccg     360
ttcttcactc cggcggagat ttctaaacaa gccaaagcct ccgcggcgaa actcatcgtc     420
actcaatccc gttacgtcga taaaatcaag aacctccaaa cgacggcgt tttgatcgtc       480 accaccgact ccgacgccat ccccgaaaac tgcctccgtt tctccgagtt aactcagtcc     540
gaagaaccac gagtggactc aataccggag aagatttcgc cagaagacgt cgtggcgctt     600
cctttctcat ccggcacgac gggtctcccc aaaggagtga tgctaacaca caaaggtcta     660
gtcacgagcg tggcgcagca agtcgacggc gagaatccga atctttactt caacagagac     720
gacgtgatcc tctgtgtctt gcctatgttc catatatacg ctctcaactc catcatgctc     780
tgtagtctca gagttggtgc cacgatcttg ataatgccta agttcgaaat cactctcttg     840
```

```
ttagagcaga tacaaaggtg taaagtcacg gtggctatgg tcgtgccacc gatcgtttta      900
gctatcgcga agtcgccgga gacgagaag tatgatctga gctcggttag gatggttaag      960
tctggagcag ctcctcttgg taaggagctt gaagatgcta ttagtgctaa gtttcctaac     1020
gccaagcttg gtcagggcta tgggatgaca gaagcaggtc cggtgctagc aatgtcgtta     1080
gggtttgcta aagagccgtt ccagtgaag tcaggagcat gtggtacggt ggtgaggaac      1140
gccgagatga agatacttga tccagacaca ggagattctt tgcctaggaa caaacccggc     1200
gaaatatgca tccgtggcaa ccaaatcatg aaaggctatc tcaatgaccc cttggccacg     1260
gcatcgacga tcgataaaga tggttggctt cacactggag acgtcggatt tatcgatgat     1320
gacgacgagc ttttcattgt ggatagattg aaagaactca tcaagtacaa aggatttcaa     1380
gtggctccag ctgagctaga gtctctcctc ataggtcatc cagaaatcaa tgatgttgct     1440
gtcgtcgcca tgaaggaaga agatgctggt gaggttcctg ttgcgtttgt ggtgagatcg     1500
aaagattcaa atatatccga agatgaaatc aagcaattcg tgtcaaaaca ggttgtgttt     1560
tataagagaa tcaacaaagt gttcttcact gactctattc ctaaagctcc atcagggaag     1620
atattgagga aggatctaag agcaagacta gcaaatggat taatgaacta g              1671

<210> SEQ ID NO 40
<211> LENGTH: 40
<212> TYPE: DNA
<213> ORGANISM: artificial
<220> FEATURE:
<223> OTHER INFORMATION: primer

<400> SEQUENCE: 40
gcgaattctt atgacgacac aagatgtgat agtcaatgat                             40

<210> SEQ ID NO 41
<211> LENGTH: 41
<212> TYPE: DNA
<213> ORGANISM: artificial
<220> FEATURE:
<223> OTHER INFORMATION: primer

<400> SEQUENCE: 41
gcactagtat cctagttcat taatccattt gctagtcttg c                           41

<210> SEQ ID NO 42
<211> LENGTH: 1182
<212> TYPE: DNA
<213> ORGANISM: artificial
<220> FEATURE:
<223> OTHER INFORMATION: codon optimised gene

<400> SEQUENCE: 42
atggcatccg tagaggagtt cagaaatgca cagagggcaa aggtccagc aaccatattg        60 gctattggaa cagccacccc tgatcactgt gtttatcaat ctgattacgc tgattactat      120
ttcagagtaa ctaaaagtga acatatgaca gaacttaaga aaagtttaa tagaatttgt      180 gataaatcta tgataaagaa aagatacata catctaactg aagaaatgtt agaggaacat     240
ccaaatatag gtgcatatat ggcaccatct ttgaatatta acaagaaat cataacagcc      300 gaggtaccta actaggtag agacgcagcc ttgaaagctt taaggaatg gggacaacca      360 aaatctaaga ttacacattt ggttttctgt acaacttccg gtgtcgaaat gccaggtgct      420
gattataaac tagcaaaacct attgggatta gagacctctg ttagaagagt tatgttgtat     480
catcaaggtt gttacgccgg aggtacagtg cttagaactc ctaaggattt ggcagaaaat      540
```

```
aacgccggtg ctagggtttt agtcgtctgc agtgaaatca ctgtcgtaac tttcagaggt        600
ccatcagaag atgctctaga cagtttggtc ggacaagcat tgtttggcga tggatcttcc        660
gccgtaattg taggcagcga tcctgatgtg tccattgaaa gaccactatt tcaattagtt        720
tctgctgctc aaacttttat tccaaattcc gccggtgcca tagcaggaaa cttgagagaa        780
gttggtttga cttttcattt gtggcctaat gtcccaacct taatttcaga aacatcgaa         840 aaatgcttaa ctcaagcctt tgacccattg gcataagcg actggaactc attgttttgg         900
attgctcatc caggtggtcc agcaatttta gacgcagtgg aggcaaaact aaacttagag        960
aagaaaaagt tggaagctac aagacacgtt ctatcagagt atggcaacat gagctctgcc       1020
tgcgttttat tcattctaga tgagatgagg aagaagtctt taagggtga aaaagccaca        1080 accggagaag gtttagattg gggtgttcta tttggtttcg gtcctggctt aacaattgag       1140
acagtggtgt tacactctgt tccaactgtc actaactaat ga                          1182
```

<210> SEQ ID NO 43
<211> LENGTH: 41
<212> TYPE: DNA
<213> ORGANISM: artificial
<220> FEATURE:
<223> OTHER INFORMATION: primer

<400> SEQUENCE: 43

```
gcgagctcag tttatcatta tcaatactcg ccatttcaaa g                            41
```

<210> SEQ ID NO 44
<211> LENGTH: 46
<212> TYPE: DNA
<213> ORGANISM: artificial
<220> FEATURE:
<223> OTHER INFORMATION: primer

<400> SEQUENCE: 44

```
cgtctagaat ccgtcgaaac taagttctgg tgttttaaaa ctaaaa                       46
```

<210> SEQ ID NO 45
<211> LENGTH: 44
<212> TYPE: DNA
<213> ORGANISM: artificial
<220> FEATURE:
<223> OTHER INFORMATION: primer

<400> SEQUENCE: 45

```
gcgagctcat agcttcaaaa tgtttctact cctttttac tctt                          44
```

<210> SEQ ID NO 46
<211> LENGTH: 45
<212> TYPE: DNA
<213> ORGANISM: artificial
<220> FEATURE:
<223> OTHER INFORMATION: primer

<400> SEQUENCE: 46

```
cgtctagaaa acttagatta gattgctatg ctttctttct aatga                        45
```

<210> SEQ ID NO 47
<211> LENGTH: 50
<212> TYPE: DNA
<213> ORGANISM: artificial
<220> FEATURE:
<223> OTHER INFORMATION: primer

<400> SEQUENCE: 47

```
ttgcgtattg ggcgctcttc cgagctcagt ttatcattat caatactcgc         50
```

<210> SEQ ID NO 48
<211> LENGTH: 35
<212> TYPE: DNA
<213> ORGANISM: artificial
<220> FEATURE:
<223> OTHER INFORMATION: primer

<400> SEQUENCE: 48

```
atggatcctc tagaatccgt cgaaactaag ttctg                         35
```

<210> SEQ ID NO 49
<211> LENGTH: 41
<212> TYPE: DNA
<213> ORGANISM: artificial
<220> FEATURE:
<223> OTHER INFORMATION: primer

<400> SEQUENCE: 49

```
atgaattctc tagaaaactt agattagatt gctatgcttt c                  41
```

<210> SEQ ID NO 50
<211> LENGTH: 44
<212> TYPE: DNA
<213> ORGANISM: artificial
<220> FEATURE:
<223> OTHER INFORMATION: primer

<400> SEQUENCE: 50

```
tgataatgat aaactgagct cggaagagcg cccaatacgc aaac               44
```

<210> SEQ ID NO 51
<211> LENGTH: 41
<212> TYPE: DNA
<213> ORGANISM: artificial
<220> FEATURE:
<223> OTHER INFORMATION: primer

<400> SEQUENCE: 51

```
atgaattctc tagaaaactt agattagatt gctatgcttt c                  41
```

<210> SEQ ID NO 52
<211> LENGTH: 35
<212> TYPE: DNA
<213> ORGANISM: artificial
<220> FEATURE:
<223> OTHER INFORMATION: primer

<400> SEQUENCE: 52

```
atggatcctc tagaatccgt cgaaactaag ttctg                         35
```

<210> SEQ ID NO 53
<211> LENGTH: 1373
<212> TYPE: DNA
<213> ORGANISM: artificial
<220> FEATURE:
<223> OTHER INFORMATION: fused gene fragments

<400> SEQUENCE: 53

```
atgaattctc tagaaaactt agattagatt gctatgcttt ctttctaatg agcaagaagt    60
aaaaaaagtt gtaatagaac aagaaaaatg aaactgaaac ttgagaaatt gaagaccgtt   120
tattaactta aatatcaatg ggaggtcatc gaaagagaaa aaaatcaaaa aaaaaatttt   180
caagaaaaag aaacgtgata aaaattttta ttgcctttttt cgacgaagaa aaagaaacga   240
```

```
ggcggtctct tttttctttt ccaaacctttt agtacgggta attaacgaca ccctagagga      300
agaaagaggg gaaatttagt atgctgtgct tgggtgtttt gaagtggtac ggcgatgcgc      360
ggagtccgag aaaatctgga agagtaaaaa aggagtagaa acattttgaa gctatgagct      420
ccagcttttg ttcccttag tgaggggtaa ttgcgcgctt ggcgtaatca tggtcatagc      480
```

```
ggcggtctct tttttctttt ccaaacctttt agtacgggta attaacgaca ccctagagga      300
agaaagaggg gaaatttagt atgctgtgct tgggtgtttt gaagtggtac ggcgatgcgc      360
ggagtccgag aaaatctgga agagtaaaaa aggagtagaa acattttgaa gctatgagct      420
ccagcttttg ttccctttag tgaggggtaa ttgcgcgctt ggcgtaatca tggtcatagc      480
tgtttcctgt gtgaaattgt tatccgctca cattccaca caacatagga gccggaagca      540
taaagtgtaa agcctggggt gcctaatgag tgaggtaact cacattaatt gcgttgcgct      600
cactgcccgc tttccagtcg gaaacctgt cgtgccagct gcattaatga atcggccaac      660
gcgcggggag aggcggtttg cgtattgggc gctcttccga gctcagttta tcattatcaa      720
tactcgccat ttcaaagaat acgtaaataa ttaatagtag tgattttcct aactttattt      780
agtcaaaaaa ttagccttttt aattctgctg taacccgtac atgcccaaaa tagggggcgg      840
gttacacaga atatataaca tcgtaggtgt ctgggtgaac agtttattcc tggcatccac      900
taaatataat gggagccgct ttttaagctg gcatccagaa aaaaaagaa tcccagcacc      960 aaaatattgt tttcttcacc aaccatcagt tcataggtcc attctcttag cgcaactaca     1020
gagaacaggg gcacaaacag gcaaaaaacg ggcacaaccct caatggagtg atgcaacctg     1080
cctggagtaa atgatgacac aaggcaattg acccacgcat gtatctatct cattttctta     1140
caccttctat taccttctgc tctctctgat ttggaaaaag ctgaaaaaaa aggttgaaac     1200
cagttccctg aaattattcc cctacttgac taataagtat ataaagacgg taggtattga     1260
ttgtaattct gtaaatctat ttcttaaact tcttaaattc tacttttata gttagtcttt     1320
tttttagttt taaaacacca gaacttagtt tcgacggatt ctagaggatc cat            1373
```

<210> SEQ ID NO 54
<211> LENGTH: 41
<212> TYPE: DNA
<213> ORGANISM: artificial
<220> FEATURE:
<223> OTHER INFORMATION: primer

<400> SEQUENCE: 54
atggatcctc tagaaaactt agattagatt gctatgcttt c                             41

<210> SEQ ID NO 55
<211> LENGTH: 36
<212> TYPE: DNA
<213> ORGANISM: artificial
<220> FEATURE:
<223> OTHER INFORMATION: primer

<400> SEQUENCE: 55
atgaattctc tagaatccgt cgaaactaag ttctgg                                  36

<210> SEQ ID NO 56
<211> LENGTH: 8832
<212> TYPE: DNA
<213> ORGANISM: artificial
<220> FEATURE:
<223> OTHER INFORMATION: vector

<400> SEQUENCE: 56
gacgaaaggg cctcgtgata cgcctatttt tataggttaa tgtcatgata ataatggttt       60
cttagtatga tccaatatca aaggaaatga tagcattgaa ggatgagact aatccaattg      120
aggagtggca gcatatagaa cagctaaagg gtagtgctga aggaagcata cgatacccccg     180 catggaatgg gataatatca caggaggtac tagactacct ttcatcctac ataaatagac      240
```

```
gcatataagt acgcatttaa gcataaacac gcactatgcc gttcttctca tgtatatata    300
tatacaggca acacgcagat ataggtgcga cgtgaacagt gagctgtatg tgcgcagctc    360
gcgttgcatt ttcggaagcg ctcgttttcg gaaacgcttt gaagttccta ttccgaagtt    420
cctattctct agaaagtata ggaacttcag agcgcttttg aaaaccaaaa gcgctctgaa    480
gacgcacttt caaaaaacca aaacgcacc ggactgtaac gagctactaa aatattgcga    540
ataccgcttc cacaaacatt gctcaaaagt atctctttgc tatatatctc tgtgctatat    600
ccctatataa cctacccatc caccttttcgc tccttgaact tgcatctaaa ctcgacctct    660
acattttta tgtttatctc tagtattact ctttagacaa aaaaattgta gtaagaacta    720
ttcatagagt gaatcgaaaa caatacgaaa atgtaaacat ttcctatacg tagtatatag    780
agacaaaata gaagaaaccg ttcataattt tctgaccaat gaagaatcat caacgctatc    840
actttctgtt cacaaagtat gcgcaatcca catcggtata gaatataatc ggggatgcct    900
ttatcttgaa aaaatgcacc cgcagcttcg ctagtaatca gtaaacgcgg gaagtggagt    960
caggcttttt ttatggaaga gaaaatagac accaaagtag ccttcttcta accttaacgg   1020
acctacagtg caaaaagtta tcaagagact gcattataga gcgcacaaag gagaaaaaaa   1080
gtaatctaag atgctttgtt agaaaaatag cgctctcggg atgcattttt gtagaacaaa   1140
aaagaagtat agattctttg ttggtaaaat agcgctctcg cgttgcattt ctgttctgta   1200
aaaatgcagc tcagattctt tgtttgaaaa attagcgctc tcgcgttgca ttttttgtttt   1260
acaaaaatga agcacagatt cttcgttggt aaaatagcgc tttcgcgttg catttctgtt   1320
ctgtaaaaat gcagctcaga ttctttgttt gaaaaattag cgctctcgcg ttgcattttt   1380
gttctacaaa atgaagcaca gatgcttcgt tcaggtggca ctttttcgggg aaatgtgcgc   1440
ggaacccta tttgttttatt tttctaaata cattcaaata tgtatccgct catgagacaa   1500
taaccctgat aaatgcttca ataatattga aaaaggaaga gtatgagtat tcaacatttc   1560
cgtgtcgccc ttattccctt ttttgcggca ttttgccttc ctgtttttgc tcacccagaa   1620
acgctggtga agtaaaaga tgctgaagat cagttgggtg cacgagtggg ttacatcgaa   1680
ctggatctca acagcggtaa gatccttgag agttttcgcc ccgaagaacg ttttccaatg   1740
atgagcactt ttaaagttct gctatgtggc gcggtattat cccgtattga cgccgggcaa   1800
gagcaactcg gtcgccgcat acactattct cagaatgact tggttgagta ctcaccagtc   1860
acagaaaagc atcttacgga tggcatgaca gtaagagaat tatgcagtgc tgccataacc   1920
atgagtgata acactgcggc caacttactt ctgacaacga tcggaggacc gaaggagcta   1980
accgcttttt tgcacaacat gggggatcat gtaactcgcc ttgatcgttg ggaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcattttaa   2460
tttaaaagga tctaggtgaa gatcctttt gataatctca tgaccaaaat cccttaacgt   2520
gagttttcgt tccactgagc gtcagacccc gtagaaaaga tcaaaggatc ttcttgagat   2580
cctttttttc tgcgcgtaat ctgctgcttg caaacaaaaa aaccaccgct accagcggtg   2640
```

```
gtttgtttgc cggatcaaga gctaccaact cttttccga aggtaactgg cttcagcaga    2700
gcgcagatac caaatactgt ccttctagtg tagccgtagt taggccacca cttcaagaac    2760
tctgtagcac cgcctacata cctcgctctg ctaatcctgt taccagtggc tgctgccagt    2820
ggcgataagt cgtgtcttac cgggttggac tcaagacgat agttaccgga taaggcgcag    2880
cggtcgggct gaacgggggg ttcgtgcaca gcccagct tggagcgaac gacctacacc      2940
gaactgagat acctcagcg tgagctatga aaagcgcca cgcttcccga agggagaaag      3000
gcggacaggt atccggtaag cggcagggtc ggaacaggag agcgcacgag ggagcttcca    3060
gggggaaacg cctggtatct ttatagtcct gtcgggtttc gccacctctg acttgagcgt    3120
cgattttgt gatgctcgtc aggggggcgg agcctatgga aaaacgccag caacgcggcc    3180
ttttacggt tcctggcctt ttgctggcct tttgctcaca tgttctttcc tgcgttatcc     3240
cctgattctg tggataaccg tattaccgcc tttgagtgag ctgataccgc tcgccgcagc    3300
cgaacgaccg agcgcagcga gtcagtgagc gaggaagcgg aagagcgccc aatacgcaaa    3360
ccgcctctcc ccgcgcgttg gccgattcat taatgcagct ggatcttcga gcgtcccaaa    3420
accttctcaa gcaaggtttt cagtataatg ttacatgcgt acacgcgtct gtacagaaaa    3480
aaaagaaaaa tttgaaatat aaataacgtt cttaatacta acataactat aaaaaaataa    3540
atagggaccct agacttcagg ttgtctaact ccttcctttt cggttagagc ggatcttagc    3600
tagccgcggt accaagctta ctcgaggtct tcttcggaaa tcaacttctg ttccatgtcg    3660
acgcccgggc cctatagtga gtcgtattac ggatcctcta gaaaacttag attagattgc    3720
tatgctttct ttctaatgag caagaagtaa aaaaagttgt aatagaacaa gaaaaatgaa    3780
actgaaactt gagaaaattga agaccgttta ttaacttaaa tatcaatggg aggtcatcga    3840
aagagaaaaa aatcaaaaaa aaaatttttca agaaaagaa acgtgataaa aattttttatt   3900
gcctttttcg acgaagaaaa agaaacgagg cggtctcttt tttctttttcc aaaccttttag  3960
tacgggtaat taacgacacc ctagaggaag aaagaggggga aatttagtat gctgtgcttg   4020
ggtgttttga agtggtacgg cgatgcgcgg agtccgagaa atctggaag agtaaaaaag    4080
gagtagaaac atttttgaagc tatgagctcc agcttttgtt ccctttagtg agggttaatt   4140
gcgcgcttgg cgtaatcatg gtcatagctg tttcctgtgt gaaattgtta tccgctcaca    4200
attccacaca acataggagc cggaagcata aagtgtaaag cctggggtgc ctaatgagtg    4260
aggtaactca cattaattgc gttgcgctca ctgcccgctt tccagtcggg aaacctgtcg    4320
tgccagctgc attaatgaat cggccaacgc gcggggagag gcggtttgcg tattgggcgc    4380
tcttccgagc tcagtttatc attatcaata ctcgccattt caaagaatac gtaaataatt    4440
aatagtagtg attttcctaa ctttatttag tcaaaaaatt agccttttaa ttctgctgta    4500
acccgtacat gcccaaaata ggggcgggt tacacagaat atataacatc gtaggtgtct     4560
gggtgaacag tttattcctg gcatccacta aatataatgg agcccgcttt ttaagctggc    4620
atccagaaaa aaaagaatc ccagcaccaa atatgtttt cttcaccaa ccatcagttc       4680
ataggtccat tctcttagcg caactacaga gaacaggggc acaaacaggc aaaaacggg     4740
cacaacctca atggagtgat gcaacctgcc tggagtaaat gatgacacaa ggcaattgac    4800
ccacgcatgt atctatctca ttttcttaca ccttctatta ccttctgctc tctctgattt    4860
ggaaaaagct gaaaaaaaag gttgaaacca gttccctgaa attattcccc tacttgacta    4920
ataagtatat aaagacggta ggtattgatt gtaattctgt aaatctattt cttaaacttc    4980
ttaaattcta cttttatagt tagtctttt tttagtttta aaacaccaga acttagtttc     5040
```

```
gacggattct agagaattcc cgatgacaca ggtagttgaa aggcaggcag ataggcttag    5100
ttccagggaa tatcttgcca gggtcgtcag gtccgctggt tgggatgctg gtttgacttc    5160
ctgtactgat gaggaaatcg tgagaatggg tgctagtgcc agaacaattg aagagtactt    5220
gaagtccgat aaacctatat acggcttaac acaaggattt ggtccacttg ttctatttga    5280
tgccgatagt gaattagagc aaggaggttc tttaatctct catctaggta caggccaagg    5340
tgctcctttg gccccagaag tgtcaagact aatcttatgg ttgagaatac agaatatgag    5400
aaaaggttat tccgcagtgt cacctgtatt ctggcagaag ttagccgatc tatggaataa    5460
gggtttcaca ccagctattc caaggcacgg tactgtctcc gcatctggcg atttgcagcc    5520
acttgctcat gctgctttag cattcactgg cgttggagaa gcatggacaa gagatgctga    5580
cggcagatgg agcactgttc ctgcagtaga cgctttggct gctttgggtg cagaaccatt    5640
tgattggcca gttagagagg cattagcttt tgttaatggt actggcgcct cattggcagt    5700
agccgtgcta aaccatagga gtgctttaag attagtgaga gcctgtgccg tgttgtccgc    5760
aaggttagcc acattgcttg gtgccaatcc tgagcattat gatgtaggtc atggcgttgc    5820
aagaggccaa gttggtcaat tgactgcagc agaatggatc aggcaaggtt tacctagagg    5880
tatggtcaga gacggaagta ggccattgca agaaccatac tccttaagat gtgctcctca    5940
agttttaggt gccgttttgg accagttaga tggagctggt gacgtattag ctagggaagt    6000
cgacggttgt caggacaatc ctataactta cgaaggagag ttgttgcatg gtggtaattt    6060
ccatgcaatg ccagttggtt tcgcatctga tcaaataggt ttagcaatgc atatggccgc    6120
ttacttggca gaaaggcagc ttggtttatt agttagccct gttacaaacg gtgaccttcc    6180
accaatgtta accccctaggg ctggtagagg cgcaggacta gcaggtgtgc agatatccgc    6240
taccagtttt gttagtagaa ttaggcagtt ggtgtttcct gcaagcttga caactttgcc    6300
taccaacgga tggaatcaag atcacgtccc aatggcattg aatggcgcaa attcagtatt    6360
cgaagcctta gagttgggat ggttaactgt tggtagcttg gcagtaggtg ttgcccaatt    6420
agccgccatg acaggtcacg ctgctgaggg tgtttgggca gaacttgctg gtatttgccc    6480
tccacttgat gctgatagac cttgggagc agaagtgagg gctgctaggg atcttttgtc    6540
tgcccacgct gatcaattgt tagtcgatga agctgatgga aaagacttcg gataatgaac    6600
tagtatcgat ggattacaag gatgacgacg ataagatctg agctcttaat taacaattct    6660
tcgccagagg tttggtcaag tctccaatca aggttgtcgg cttgtctacc ttgccagaaa    6720
tttacgaaaa gatggaaaag ggtcaaatcg ttggtagata cgttgttgac acttctaaat    6780
aagcgaattt cttatgattt atgattttta ttattaaata agttataaaa aaaataagtg    6840
tatacaaatt ttaaagtgac tcttaggttt taaaacgaaa attcttattc ttgagtaact    6900
ctttcctgta ggtcaggttg ctttctcagg tatagcatga ggtcgctcca attcagctgg    6960
cgtaatagcg aagaggcccg caccgatcgc ccttcccaac agttgcgcag cctgaatggc    7020
gaatggacgc gccctgtagc ggcgcattaa gcgcggcggg tgtggtggtt acgcgcagcg    7080
tgaccgctac acttgccagc gccctagcgc ccgctccttt cgctttcttc ccttcctttc    7140
tcgccacgtt cgccggcttt ccccgtcaag ctctaaatcg ggggctccct ttagggttcc    7200
gatttagtgc tttacggcac ctcgacccca aaaaacttga ttagggtgat ggttcacgta    7260
gtgggccatc gccctgatag acggttttc gccctttgac gttggagtcc acgttcttta    7320
atagtggact cttgttccaa actggaacaa cactcaaccc tatctcggtc tattcttttg    7380
atttataagg gattttgccg atttcggcct attggttaaa aaatgagctg atttaacaaa    7440
```

-continued

```
aatttaacgc gaattttaac aaaatattaa cgtttacaat ttcctgatgc ggtattttct    7500
ccttacgcat ctgtgcggta tttcacaccg catagggtaa taactgatat aattaaattg    7560
aagctctaat ttgtgagttt agtatacatg catttactta taatacagtt ttttagtttt    7620
gctggccgca tcttctcaaa tatgcttccc agcctgcttt tctgtaacgt tcaccctcta    7680
ccttagcatc ccttcccttt gcaaatagtc ctcttccaac aataataatg tcagatcctg    7740
tagagaccac atcatccacg gttctatact gttgacccaa tgcgtctccc ttgtcatcta    7800
aacccacacc gggtgtcata atcaaccaat cgtaaccttc atctcttcca cccatgtctc    7860
tttgagcaat aaagccgata acaaaatctt tgtcgctctt cgcaatgtca acagtaccct    7920
tagtatattc tccagtagat agggagccct tgcatgacaa ttctgctaac atcaaaaggc    7980
ctctaggttc ctttgttact tcttctgccg cctgcttcaa accgctaaca atacctgggc    8040
ccaccacacc gtgtgcattc gtaatgtctg cccattctgc tattctgtat acacccgcag    8100
agtactgcaa tttgactgta ttaccaatgt cagcaaattt tctgtcttcg aagagtaaaa    8160
aattgtactt ggcggataat gcctttagcg gcttaactgt gccctccatg gaaaaatcag    8220
tcaagatatc cacatgtgtt tttagtaaac aaattttggg acctaatgct tcaactaact    8280
ccagtaattc cttggtggta cgaacatcca atgaagcaca caagtttgtt tgcttttcgt    8340
gcatgatatt aaatagcttg gcagcaacag gactaggatg agtagcagca cgttccttat    8400
atgtagcttt cgacatgatt tatcttcgtt tcctgcaggt ttttgttctg tgcagttggg    8460
ttaagaatac tgggcaattt catgtttctt caacactaca tatgcgtata tataccaatc    8520
taagtctgtg ctccttcctt cgttcttcct tctgttcgga gattaccgaa tcaaaaaaat    8580
ttcaaagaaa ccgaaatcaa aaaaagaat aaaaaaaaaa tgatgaattg aattgaaaag    8640
ctgtggtatg gtgcactctc agtacaatct gctctgatgc cgcatagtta agccagcccc    8700
gacacccgcc aacacccgct gacgcgccct gacgggcttg tctgctcccg gcatccgctt    8760
acagacaagc tgtgaccgtc tccgggagct gcatgtgtca gaggttttca ccgtcatcac    8820
cgaaacgcgc ga                                                        8832
```

<210> SEQ ID NO 57
<211> LENGTH: 10157
<212> TYPE: DNA
<213> ORGANISM: artificial
<220> FEATURE:
<223> OTHER INFORMATION: vector

<400> SEQUENCE: 57

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctctag tacactctat attttttat gcctcggtaa tgattttcat     360
tttttttttt cccctagcgg atgactcttt tttttcttta gcgattggca ttatcacata     420
atgaattata cattatataa agtaatgtga tttcttcgaa gaatatacta aaaaatgagc     480
aggcaagata acgaaggca agatgacag agcagaaagc cctagtaaag cgtattacaa     540
atgaaaccaa gattcagatt gcgatctctt taaagggtgg tccccctagcg atagagcact     600
cgatcttccc agaaaaagag gcagaagcag tagcagaaca ggccacacaa tcgcaagtga     660
```

```
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tctttttttt tctcttgaac tcgacggatc tatgcggtgt   1380
gaaataccgc acagatgcgt aaggagaaaa taccgcatca ggaaattgta acgttaata   1440 ttttgttaaa attcgcgtta aattttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctgaattg gagcgacctc atgctatacc   1980
tgagaaagca acctgaccta caggaaagag ttactcaaga ataagaattt tcgttttaaa   2040
acctaagagt cactttaaaa tttgtataca cttatttttt ttataactta tttaataata   2100
aaaatcataa atcataagaa attcgcttat ttagaagtgt caacaacgta tctaccaacg   2160
atttgaccct tttccatctt ttcgtaaatt tctggcaagg tagacaagcc gacaaccttg   2220
attggagact tgaccaaacc tctggcgaag aattgttaat taagagctca gatcttatcg   2280
tcgtcatcct tgtaatccat cgatactagt ctagttcatt aatccatttg ctagtcttgc   2340
tcttagatcc ttcctcaata tcttccctga tggagcttta ggaatagagt cagtgaagaa   2400
cactttgttg attctcttat aaaacacaac ctgttttgac acgaattgct tgatttcatc   2460
ttcggatata tttgaatctt tcgatctcac cacaaacgca acaggaacct caccagcatc   2520
ttcttccttc atggcgacga cagcaacatc attgatttct ggatgaccta tgaggagaga   2580
ctctagctca gctggagcca cttgaaatcc tttgtacttg atgagttctt tcaatctatc   2640
cacaatgaaa agctcgtcgt catcatcgat aaatccgacg tctccagtgt gaagccaacc   2700
atctttatcg atcgtcgatg ccgtggccaa ggggtcattg agatagcctt tcatgatttg   2760
gttgccacgg atgcatattt cgccgggttt gttcctaggc aaagaatctc ctgtgtctgg   2820
atcaagtatc ttcatctcgg cgttcctcac caccgtacca catgctcctg acttcactgg   2880
aaacggctct ttagcaaacc ctaacgacat tgctagcacc ggacctgctt ctgtcatccc   2940
atagccctga ccaagcttgg cgttaggaaa cttagcacta atagcatctt caagctcctt   3000
accaagagga gctgctccag acttaaccat cctaaccgag ctcagatcat acttctccgt   3060
```

```
ctccggcgac ttcgcgatag ctaaaacgat cggtggcacg accatagcca ccgtgacttt    3120
acacctttgt atctgctcta acaagagagt gatttcgaac ttaggcatta tcaagatcgt    3180
ggcaccaact ctgagactac agagcatgat ggagttgaga gcgtatatat ggaacatagg    3240
caagacacag aggatcacgt cgtctctgtt gaagtaaaga ttcggattct cgccgtcgac    3300
ttgctgcgcc acgctcgtga ctagaccttt gtgtgttagc atcactcctt ggggagacc     3360 cgtcgtgccg gatgagaaag gaagcgccac gacgtcttct ggcgaaatct tctccggtat    3420
tgagtccact cgtggttctt cggactgagt taactcggag aaacggaggc agttttcggg    3480
gatggcgtcg gagtcggtgg tgacgatcaa acgccgtcg ttttggaggt tcttgatttt     3540
atcgacgtaa cgggattgag tgacgatgag tttcgccgcg gaggctttgg cttgtttaga    3600
aatctccgcc ggagtgaaga acgggttcgc ggaggtggtg attgcgccga tgaaggaggc    3660
ggcaaggaaa gtgaggacta cttcaggaga gttcgggagg aggatcatta caacgtcgtg    3720
ttgcttcacg ccgaggttat gaagaccggc ggcgagtttc cgagatgtta cgtggacatc    3780
ggcgtaggtg tatacttcgc cggtgggacc gttgatcaag catggcttag cggcgaactc    3840
tgagatattt tcgaagatgt agtcgtggag tgggaggtgg ttaggatgt atatatcagg     3900 caatctcgat cggaaaatga cgtcattact acactgtttc tgatcattct gatcattgac    3960
tatcacatct tgtgtcgtca tgaattctct agaaaactta gattagattg ctatgctttc    4020
tttctaatga gcaagaagta aaaaaagttg taatagaaca agaaaatga aactgaaact     4080 tgagaaattg aagaccgttt attaacttaa atatcaatgg gaggtcatcg aaagagaaaa    4140
aaatcaaaaa aaaaattttc aagaaaaaga aacgtgataa aaatttttat tgccttttc     4200 gacgaagaaa agaaacgag gcggtctctt ttttcttttc caaacccttta gtacgggtaa    4260 ttaacgacac cctagaggaa gaaagagggg aaatttagta tgctgtgctt gggtgttttg    4320
aagtggtacg gcgatgcgcg gagtccgaga aatctggaa gagtaaaaaa ggagtagaaa     4380 catttttgaag ctatgagctc cagcttttgt tccctttagt gagggttaat tgcgcgcttg    4440
gcgtaatcat ggtcatagct gtttcctgtg tgaaattgtt atccgctcac aattccacac    4500
aacataggag ccggaagcat aaagtgtaaa gcctgggggtg cctaatgagt gaggtaactc    4560
acattaattg cgttgcgctc actgcccgct ttccagtcgg gaaacctgtc gtgccagctg    4620
cattaatgaa tcggccaacg cgcggggaga ggcggtttgc gtattgggcg ctcttccgag    4680
ctcagtttat cattatcaat actcgccatt tcaaagaata cgtaaataat taatagtagt    4740
gattttccta actttatta gtcaaaaaat tagccttta attctgctgt aacccgtaca      4800
tgcccaaaat agggggcggg ttacacagaa tatataacat cgtaggtgtc tgggtgaaca    4860
gtttattcct ggcatccact aaatataatg gagcccgctt tttaagctgg catccagaaa    4920 aaaaagaat cccagcacca aaatattgtt ttcttcacca accatcagtt cataggtcca     4980
ttctcttagc gcaactacag agaacagggg cacaaacagg caaaaaacgg gcacaacctc    5040
aatggagtga tgcaacctgc ctggagtaaa tgatgacaca aggcaattga cccacgcatg    5100
tatctatctc attttcttac accttctatt accttctgct ctctctgatt tggaaaaagc    5160
tgaaaaaaaa ggttgaaacc agttccctga aattattccc ctacttgact aataagtata    5220 taaagacgg aggtattgat tgtaattctg taaatctatt tcttaaactt cttaaattct     5280
acttttatag ttagtctttt ttttagtttt aaaacaccag aacttagttt cgacggattc    5340
tagaggatcc atggcatccg tagaggagtt cagaaatgca cagagggcaa aaggtccagc    5400
aaccatattg gctattggaa cagccacccc tgatcactgt gtttatcaat ctgattacgc    5460
```

| | |
|---|---|
| tgattactat ttcagagtaa ctaaaagtga acatatgaca gaacttaaga aaaagtttaa | 5520 |
| tagaatttgt gataaatcta tgataaagaa aagatacata catctaactg aagaaatgtt | 5580 |
| agaggaacat ccaaatatag gtgcatatat ggcaccatct ttgaatatta gacaagaaat | 5640 |
| cataacagcc gaggtaccta gactaggtag agacgcagcc ttgaaagctt taaggaatg | 5700 |
| gggacaacca aaatctaaga ttacacattt ggttttctgt acaacttccg gtgtcgaaat | 5760 |
| gccaggtgct gattataaac tagcaaacct attgggatta gagacctctg ttagaagagt | 5820 |
| tatgttgtat catcaaggtt gttacgccgg aggtacagtg cttagaactg ctaaggattt | 5880 |
| ggcagaaaat aacgccggtg ctagggtttt agtcgtctgc agtgaaatca ctgtcgtaac | 5940 |
| tttcagaggt ccatcagaag atgctctaga cagtttggtc ggacaagcat tgtttggcga | 6000 |
| tggatcttcc gccgtaattg taggcagcga tcctgatgtg tccattgaaa gaccactatt | 6060 |
| tcaattagtt tctgctgctc aaacttttat tccaaattcc gccggtgcca tagcaggaaa | 6120 |
| cttgagagaa gttggtttga cttttcattt gtggcctaat gtcccaacct taatttcaga | 6180 |
| aaacatcgaa aaatgcttaa ctcaagcctt tgacccattg gcataagcg actggaactc | 6240 |
| attgttttgg attgctcatc caggtggtcc agcaatttta gacgcagtgg aggcaaaact | 6300 |
| aaacttagag aagaaaaagt tggaagctac aagacacgtt ctatcagagt atggcaacat | 6360 |
| gagctctgcc tgcgttttat tcattctaga tgagatgagg aagaagtctt taagggtga | 6420 |
| aaaagccaca accggagaag gttagattg gggtgttcta tttggtttcg gtcctggctt | 6480 |
| aacaattgag acagtggtgt tacactctgt tccaactgtc actaactaat gactcgagta | 6540 |
| agcttggtac cgcggctagc taagatccgc tctaaccgaa aaggaaggag ttagacaacc | 6600 |
| tgaagtctag gtccctattt atttttttat agttatgtta gtattaagaa cgttatttat | 6660 |
| atttcaaatt tttcttttt ttctgtacag acgcgtgtac gcatgtaaca ttatactgaa | 6720 |
| aaccttgctt gagaaggttt tgggacgctc gaagatccag ctgcattaat gaatcggcca | 6780 |
| acgcgcgggg agaggcggtt tgcgtattgg gcgctcttcc gcttcctcgc tcactgactc | 6840 |
| gctgcgctcg tcgttcggc tgcggcgagc ggtatcagct cactcaaagg cggtaatacg | 6900 |
| gttatccaca gaatcagggg ataacgcagg aaagaacatg tgagcaaaag gccagcaaaa | 6960 |
| ggccaggaac cgtaaaaagg ccgcgttgct ggcgtttttc cataggctcc gcccccctga | 7020 |
| cgagcatcac aaaaatcgac gctcaagtca gaggtggcga aacccgacag gactataaag | 7080 |
| ataccaggcg tttccccctg gaagctccct cgtgcgctct cctgttccga ccctgccgct | 7140 |
| taccggatac ctgtccgcct ttctcccttc gggaagcgtg gcgctttctc atagctcacg | 7200 |
| ctgtaggtat ctcagttcgg tgtaggtcgt tcgctccaag ctgggctgtg tgcacgaacc | 7260 |
| ccccgttcag cccgaccgct gcgccttatc cggtaactat cgtcttgagt ccaacccggt | 7320 |
| aagacacgac ttatcgccac tggcagcagc cactggtaac aggattagca gagcgaggta | 7380 |
| tgtaggcggt gctacagagt tcttgaagtg gtggcctaac tacggctaca ctagaaggac | 7440 |
| agtatttggt atctgcgctc tgctgaagcc agttaccttc ggaaaaagag ttggtagctc | 7500 |
| ttgatccggc aaacaaacca ccgctggtag cggtggtttt tttgtttgca agcagcagat | 7560 |
| tacgcgcaga aaaaaggat ctcaagaaga tcctttgatc ttttctacgg ggtctgacgc | 7620 |
| tcagtggaac gaaaactcac gttaagggat tttggtcatg agattatcaa aaaggatctt | 7680 |
| cacctagatc cttttaaatt aaaaatgaag ttttaaatca atctaaagta tatatgagta | 7740 |
| aacttggtct gacagttacc aatgcttaat cagtgaggca cctatctcag cgatctgtct | 7800 |
| atttcgttca tccatagttg cctgactccc cgtcgtgtag ataactacga tacgggaggg | 7860 |

-continued

```
cttaccatct ggccccagtg ctgcaatgat accgcgagac ccacgctcac cggctccaga   7920
tttatcagca ataaaccagc cagccggaag ggccgagcgc agaagtggtc ctgcaacttt   7980
atccgcctcc atccagtcta ttaattgttg ccgggaagct agagtaagta gttcgccagt   8040
taatagtttg cgcaacgttg ttgccattgc tacaggcatc gtggtgtcac gctcgtcgtt   8100
tggtatggct tcattcagct ccggttccca acgatcaagg cgagttacat gatccccat    8160
gttgtgcaaa aaagcggtta gctccttcgg tcctccgatc gttgtcagaa gtaagttggc   8220
cgcagtgtta tcactcatgg ttatggcagc actgcataat tctcttactg tcatgccatc   8280
cgtaagatgc ttttctgtga ctggtgagta ctcaaccaag tcattctgag aatagtgtat   8340
gcggcgaccg agttgctctt gcccggcgtc aatacgggat aataccgcgc cacatagcag   8400
aactttaaaa gtgctcatca ttggaaaacg ttcttcgggg cgaaaactct caaggatctt   8460
accgctgttg agatccagtt cgatgtaacc cactcgtgca cccaactgat cttcagcatc   8520
ttttactttc accagcgttt ctgggtgagc aaaaacagga aggcaaaatg ccgcaaaaaa   8580
gggaataagg gcgacacgga aatgttgaat actcatactc ttcctttttc aatattattg   8640
aagcatttat cagggttatt gtctcatgag cggatacata tttgaatgta tttagaaaaa   8700
taaacaaata ggggttccgc gcacatttcc ccgaaaagtg ccacctgaac gaagcatctg   8760
tgcttcattt tgtagaacaa aaatgcaacg cgagagcgct aatttttcaa acaaagaatc   8820
tgagctgcat ttttacagaa cagaaatgca acgcgaaagc gctatttac caacgaagaa    8880
tctgtgcttc atttttgtaa aacaaaaatg caacgcgaga cgctaatttt tcaaacaaa    8940
gaatctgagc tgcattttta cagaacagaa atgcaacgcg agagcgctat tttaccaaca   9000
aagaatctat acttctttt tgttctacaa aaatgcatcc cgagagcgct attttttctaa   9060
caaagcatct tagattactt tttttctcct ttgtgcgctc tataatgcag tctcttgata   9120
acttttttgca ctgtaggtcc gttaaggtta gaagaaggct actttggtgt ctattttctc   9180
ttccataaaa aaagcctgac tccacttccc gcgtttactg attactagcg aagctgcggg   9240
tgcatttttt caagataaag gcatccccga ttatattcta taccgatgtg gattgcgcat   9300
actttgtgaa cagaaagtga tagcgttgat gattcttcat tggtcagaaa attatgaacg   9360
gtttcttcta ttttgtctct atatactacg tataggaaat gtttacattt tcgtattgtt   9420
ttcgattcac tctatgaata gttcttacta caatttttt gtctaaagag taatactaga    9480
gataaacata aaaaatgtag aggtcgagtt tagatgcaag ttcaaggagc gaaaggtgga   9540
tgggtaggtt atatagggat atagcacaga gatatatagc aaagagatac ttttgagcaa   9600
tgtttgtgga agcggtattc gcaatatttt agtagctcgt tacagtccgg tgcgtttttg   9660
gttttttgaa agtgcgtctt cagagcgctt ttggttttca aaagcgctct gaagttccta   9720
tactttctag agaataggaa cttcggaata ggaacttcaa agcgtttccg aaaacgagcg   9780
cttccgaaaa tgcaacgcga gctgcgcaca tacagctcac tgttcacgtc gcacctatat   9840
ctgcgtgttg cctgtatata tatatacatg agaagaacgg catagtgcgt gtttatgctt   9900
aaatgcgtac ttatatgcgt ctatttatgt aggatgaaag gtagtctagt acctcctgtg   9960
atattatccc attccatgcg gggtatcgta tgcttccttc agcactaccc tttagctgtt  10020
ctatatgctg ccactcctca attggattag tctcatcctt caatgctatc atttcctttg  10080
atattggatc atctaagaaa ccattattat catgacatta acctataaaa ataggcgtat  10140
cacgaggccc tttcgtc                                                 10157
```